US012551610B2

(12) United States Patent
Swift et al.

(10) Patent No.: US 12,551,610 B2
(45) Date of Patent: Feb. 17, 2026

(54) ILLUMINATED SUCTION DEVICE

(71) Applicant: CooperSurgical, Inc., Trumbull, CT (US)

(72) Inventors: Jason Swift, Newburyport, MA (US); Matthew Traub, Andover, MA (US); James Pehl, Salem, NH (US); Adrienne Clark, Arlington, MA (US); Steven Meyer, Arlington, MA (US); Kate Leslie, Burlington, MA (US)

(73) Assignee: CooperSurgical, Inc., Trumbull, CT (US)

( * ) Notice: Subject to any disclaimer, the term of this patent is extended or adjusted under 35 U.S.C. 154(b) by 0 days.

(21) Appl. No.: 18/648,826

(22) Filed: Apr. 29, 2024

(65) Prior Publication Data

US 2025/0127981 A1 Apr. 24, 2025

Related U.S. Application Data

(60) Provisional application No. 63/591,858, filed on Oct. 20, 2023.

(51) Int. Cl.
*A61M 1/00* (2006.01)
*A61B 90/30* (2016.01)
(Continued)

(52) U.S. Cl.
CPC ............... *A61M 1/84* (2021.05); *A61B 90/30* (2016.02); *A61M 1/71* (2021.05); *A61M 1/74* (2021.05); *A61M 1/76* (2021.05); *A61M 1/87* (2021.05); *A61B 2090/308* (2016.02); *A61M 2205/3633* (2013.01); *A61M 2205/587* (2013.01); *F21V 5/04* (2013.01); *F21V 29/70* (2015.01); *F21V 33/0068* (2013.01); *F21W 2131/20* (2013.01)

(58) Field of Classification Search
CPC ............ A61M 1/71; A61M 1/74; A61M 1/76; A61M 1/84; A61M 1/87; A61M 2205/3633; A61M 2205/587; A61M 2205/586; A61B 90/30; A61B 2090/308; F21V 5/04; F21V 29/70; F21V 33/0068; F21W 2131/20
See application file for complete search history.

(56) References Cited

U.S. PATENT DOCUMENTS

| | | | | |
|---|---|---|---|---|
| 9,114,202 | B1 * | 8/2015 | Huttner .................. | A61B 1/018 |
| 10,512,519 | B2 | 12/2019 | Swift et al. | |

(Continued)

OTHER PUBLICATIONS

International Search Report and Written Opinion in International Appln. No. PCT/US2024/051411, mailed on Feb. 10, 2025, 21 pages.

*Primary Examiner* — Kami A Bosworth
*Assistant Examiner* — Avery Smale
(74) *Attorney, Agent, or Firm* — Fish & Richardson P.C.

(57) ABSTRACT

A suction device comprising a suction tube configured to fluidly couple to a vacuum source and to provide suction at its distal end, an illumination assembly comprising at least one direct light source for emitting light to a target area, an elongated heat sink thermally coupled to the at least one light source and extending along a portion of the suction tube, and a spine extending along the suction tube and overlapping with the elongated heat sink, the spine including an integrated lens, wherein the at least one direct light source and the elongated heat sink are enclosed within a space formed between the spine and a side of the suction tube.

20 Claims, 15 Drawing Sheets

(51) Int. Cl.

| | |
|---|---|
| ***F21V 5/04*** | (2006.01) |
| ***F21V 29/70*** | (2015.01) |
| ***F21V 33/00*** | (2006.01) |
| ***F21W 131/20*** | (2006.01) |

(56) References Cited

U.S. PATENT DOCUMENTS

| | | | | |
|---|---|---|---|---|
| 10,722,621 | B2 | 7/2020 | Swift | |
| 10,959,609 | B1 * | 3/2021 | Swift | A61B 1/0684 |
| 2006/0291195 | A1 | 12/2006 | Horrell et al. | |
| 2008/0266840 | A1 | 10/2008 | Nordmeyer et al. | |
| 2013/0294068 | A1 * | 11/2013 | Kuenzler | F21V 29/74 362/234 |
| 2015/0297069 | A1 * | 10/2015 | Coppersmith | A61B 1/0676 600/249 |
| 2019/0254771 | A1 | 8/2019 | Swift et al. | |

* cited by examiner

100

ILLUMINATED SUCTION DEVICE

RELATED APPLICATIONS

The present application claims priority to U.S. Provisional Application No. 63/591,858 filed on Oct. 20, 2023. The entire disclosure of this provisional application is incorporated herein by reference.

FIELD OF THE INVENTION

Embodiments described herein relate to a surgical instrument with a compact, low-profile illumination assembly for improved lighting and heat dissipation features. The surgical instrument described in the illustrative embodiments herein is especially well suited for the removal of body fluids such as blood from a surgical wound and for simultaneously illuminating an area of the wound so that the same can be visualized by a surgeon. In addition, the surgical instrument includes a controller for controlling both suction amount and illumination by the illumination assembly incorporated into an ergonomic handle.

INTRODUCTION

It is often necessary during the course of a surgical procedure for body fluids, such as blood, to be removed from the area of the surgical wound or incision in order to allow visualization by a surgeon. In addition, it is often necessary to maintain a surgical suction device in place in the wound or within the incision in order to permit a surgeon to visualize the point at which the bleeding has occurred. Particularly when such a suction device is in place, it is extremely difficult and often impossible to prevent the suction device from interfering with the desired visualization and illumination.

Hand-held suction devices are routinely used during surgical procedures. These devices are typically connected to a standard suction source in the operating room, enabling the physician to dynamically and efficiently remove blood, bone fragments, or fluid previously irrigated into the surgical site. These suction devices are sometimes also used to provide low force retraction of fat, muscle, or other structures during the procedure. A surgeon holds the suction device from its proximal end, manipulating the distal portion of the suction device during the surgical procedure in order to provide suction at the desired location. Hand-held suction devices are widely available in a variety of configurations suited to various surgical applications. For example, Yankauer suction devices typically have large lumens to provide rapid aspiration and resist clogging and are usually used for surface suction and intra-abdominal suction; Frazier suction devices typically have control vents to allow suction control and are used in open surgical procedures where fine, delicate suctioning is needed to evacuate fluid and debris from the surgical site; Poole suction devices are designed for use in abdominal surgeries and cesarean sections to evacuate pooled blood, fluids and debris; and Sigmoid suction devices are usually used for sigmoidoscopy and colonoscopy procedures to evacuate blood, fluids and debris. These suction devices typically include a port or a tail end that is configured to connect to a tubing which provides suction and that can work with suction machine devices, and a tip end which is inserted into an area to be evacuated. Different style tips may be used with the suction devices to provide tailored suction.

During use of a suction device, visualization of the wound or surgical site is often greatly improved by providing illumination inside the wound or into the surgical site. Some conventional illuminated surgical devices have illumination supplied by a fiber-optic light guide connected to the device, with light guided through the light guide to an aperture near the distal end of the suction device, from which the light is directed toward the surgical field. These suction devices are constrained by the need for an umbilical cord, i.e., light guide, tethering it to a large, heavy, expensive, relatively non-portable, AC-powered light source. In addition, the limited flexibility of the light guide tends to hamper the use of the tool by the surgeon.

Other suction devices include illumination supplied by a LED installed on the instrument and powered by batteries, with luminance from the LED being aimed toward the surgical field. U.S. Pat. Nos. 10,722,621 and 10,959,609, both assigned to the same assignee herein and incorporated herein by reference, are examples of illuminated suction devices falling into the second category. The ’621 patent discloses a suction device with at least one LED coupled suction tube of the device, primarily to the top position on the suction tube, with the LED emitting light directly to the target area in front of a tip of the suction tube. The ’609 patent discloses an illuminated suction device that incorporates multiple LEDs positioned around the suction tube of the device, and also includes heat dissipation features. These illuminated suction devices are capable of providing bright illumination to a target area within the wound or incision without being constrained by the need for an outside light source or an external power source.

SUMMARY OF THE INVENTION

The present invention provides an improved illuminated medical device, such as a Frazier suction device, which provides an improved illuminance pattern to a target area with improved brightness, and which includes heat dissipation features. The illuminated suction device of the present invention incorporates these features in a small size package that minimizes an increase in the size of the distal end of the device due to the illumination assembly and avoids interference with the operators view of the target area. In addition, the illuminated suction device includes improved ergonomic control for controlling the illumination assembly and may or may not include control for controlling the amount of suction to be applied.

In accordance with one embodiment of the present invention, a suction device includes a suction tube configured to fluidly couple to a vacuum source and to provide suction at its distal end, an illumination assembly comprising at least one direct light source for emitting light to a target area, an elongated heat sink thermally coupled to the at least one light source and extending along a portion of the suction tube, and a spine extending along the suction tube and overlapping with the elongated heat sink, the spine including an integrated lens or a separately formed lens. In this embodiment, the at least one direct light source and the elongated heat sink are enclosed within a space formed between the spine and a side of the suction tube. In certain embodiments, the spine is transparent or translucent. The lens may be integrated into a distal end of the spine or connected to the distal end of the spine and is configured to refract light emitted from the at least one direct light source toward the target area. In some embodiments, the lens is an aspherical lens.

In certain embodiments, the spine includes an elongated channel and wherein the at least one direct light source and the elongated heat sink are positioned within the elongated channel. In some embodiments, the direct light source is mounted on a flexible circuit including electrical connections and the flexible circuit wraps around the elongated heat sink to position the direct light source adjacent a distal end of the elongated heat sink. In one exemplary configuration, the direct light source is mounted on the flexible circuit at a predetermined distance from a first free end of the flexible circuit, the first free end of the flexible circuit and a first portion of the flexible circuit extend along a first surface of the elongated heat sink, and a second portion of the flexible circuit extends along a second, opposing surface of the elongated heat sink, and the second portion of the flexible circuit electrically connects the direct light source to a power source.

In some embodiments, the elongated heat sink includes one of a recess and a projection in a first surface and the spine includes another one of the recess and the projection on its inner surface abutting the first surface of the elongated heat sink, with the projection being positioned so as to engage with the recess.

In some configurations, the suction device also includes a power source, a control assembly for controlling the operation of the illumination assembly, and a handle enclosing a proximal end of the suction tube and at least partially enclosing the power source and the control assembly. In some embodiments, the suction device includes an outer housing that encloses at least a portion of the spine and a portion of the suction tube.

An illumination assembly for use in a medical device is also described. The illumination assembly includes at least one direct light source for emitting light transmitted to a target area, an elongated heat sink thermally coupled to the at least one light source and configured to extend along a portion of an operative portion of the medical device, and a spine configured to extend along a portion of the operative portion of the medical device and overlapping with the elongated heat sink, the spine including an integrated lens and an elongated channel formed along its length. In the illumination assembly, the at least one direct light source and the elongated heat sink are positioned within the elongated channel in the spine and when the illumination assembly is attached to the medical device, the at least one light source and the elongated heat sink are enclosed between the spine and a side of the operative portion of the medical device. The illumination assembly includes features similar to those of the suction device.

In accordance with some embodiments of the invention, the illumination suction device includes a suction tube configured to fluidly couple to a vacuum source and to provide suction at its distal end, an ergonomic handle enclosing a portion of the suction tube, at least one direct light source for emitting light to a target area, and an integrated controller including a suction control portion for controlling amount of suction through the suction tube and an operation member for controlling operation of the at least one direct light source. The integrated controller is accommodated within the handle to provide ergonomic one-hand control using the suction control portion and the operation member.

In some embodiments, the handle includes a recessed concave portion and the integrated controller is accommodated in the recessed concave portion to provide tactile guidance to a user to the suction control portion and the operation member. The suction control portion may include a tear-shaped opening in fluid communication with a through opening in the suction tube and a concave peripheral portion around the tear-shaped opening. In some embodiments, the concave peripheral portion is oval-shaped to accommodate a user's finger and to provide tactile guidance to the tear-shaped opening.

In certain embodiments, the integrated controller is overmolded around the suction tube. The integrated controller may be formed as a single-piece member having an elongated arm extending from the suction control portion and the operation member provided on the elongated arm. In one illustrative configuration, the elongated arm is configured to move within the handle when the operation member is operated by a user, and the elongated arm includes an activation portion that causes activation or deactivation of the light source when the operation member is operated by a user.

In accordance with the present invention, an illumination assembly for use in a medical device is provided that includes at least one direct light source for emitting light transmitted to a target area, a heat sink thermally connected to the at least one light source and forming a spine configured to extend along a portion of the operative portion of the medical device, and a lens connected to the spine for refracting light emitted from the at least one direct light source, wherein the at least one direct light source is positioned between the lens and the spine. A suction device that includes the illumination assembly is also described, wherein the operative portion is a suction tube configured to fluidly couple to a vacuum source and to provide suction at its distal end.

Various arrangements and features of the invention are contemplated and described herein below.

BRIEF DESCRIPTION OF THE DRAWINGS

The above and other features and aspects of the present invention will become more apparent upon reading the following detailed description in conjunction with the accompanying drawings, in which.

DETAILED DESCRIPTION OF EXEMPLARY EMBODIMENTS

Figure 1A:
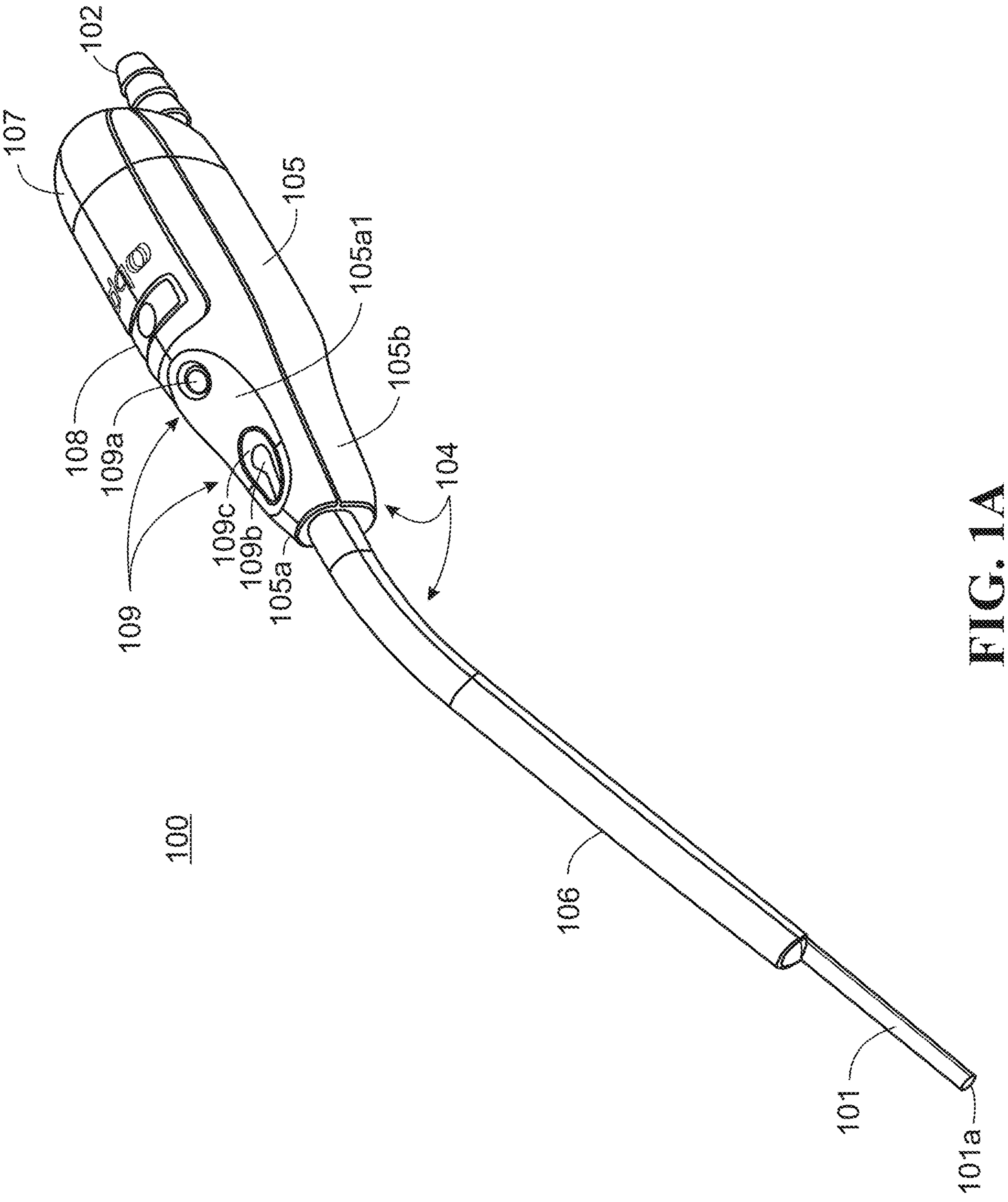
FIGS. 1A-1E show different views of the illuminated suction device of the present invention.

Drawings have been used herein to depict select exemplary embodiments. For the sake of clear illustration, many practical details are explained together in the description below. However, it should be appreciated that those details should not be used to limit the scope of any claims that issue in connection with this application. In some embodiments, certain details are not essential.

Moreover, for the sake of drawing simplification, some customary structures and elements in the drawings have been shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art. It should be further understood that terms, such as those defined in commonly used dictionaries, should be interpreted as having a meaning that is consistent with their meaning in the context of the relevant art and the present description, and should not be interpreted in an idealized or overly formal sense unless expressly so defined herein.

FIGS. 1A-1E show different views of an illustrative illuminated suction device 100 of the present invention. In FIGS. 1A-1E, the illuminated suction device 100 is a Frazier type suction device that can access small surgical sites and can provide fine and controlled suction as needed to evacuate fluids. However, it is understood that the features described below, such as the constructions of the illumination assembly and/or the controller of the suction device, can be adapted for use with other types of suction devices, such as Yankauer suction devices, Poole and Sigmoid suction devices. In addition, these features may also be adapted for use in other medical devices, including retractors, laryngoscopes, electrocautery devices, speculums and other medical devices that use illumination and/or have components that produce heat.

In accordance with the invention, the suction device 100 includes an illumination assembly with heat dissipating features which is configured to provide a targeted bright spot illumination to a target area, e.g., an area above a suction tube of the suction device and/or an area above or in front of a distal end of the suction tube. The illumination assembly has a compact, low-profile construction which does not substantially increase the overall size of the device, particularly near the distal portion of the device. The illumination assembly also does not use a waveguide or a light guide, resulting in brighter light from one or more direct light sources delivered to the target area and minimizing loss of brightness. In addition, the suction device 100 includes a controller for controlling the illumination assembly and for controlling the suction through the suction tube of the suction device. The controller is assembled together with the outer housing of the suction device to provide ergonomic construction and to provide one-handed control of the suction device, its illumination assembly and the suction through the suction device. These features are described in more detail below.

As shown in FIGS. 1A-1E, the suction device 100 includes a suction tube 101 extending between the distal end 101*a*, which is configured to be inserted into a wound or incision, and a proximal end (not visible) fluidly coupled to a barb 102 or other suitable port or connector for connecting to a suction source (not shown). The suction tube 101 in the present illustrative embodiment is curved or bent in around the central area between the distal end and the proximal end. The suction tube 101 may be formed from plastic or polymer materials, which may be opaque, transparent or translucent, or from metallic materials such as stainless steel or other non-corrosive and biocompatible metallic materials.

Figure 7A:
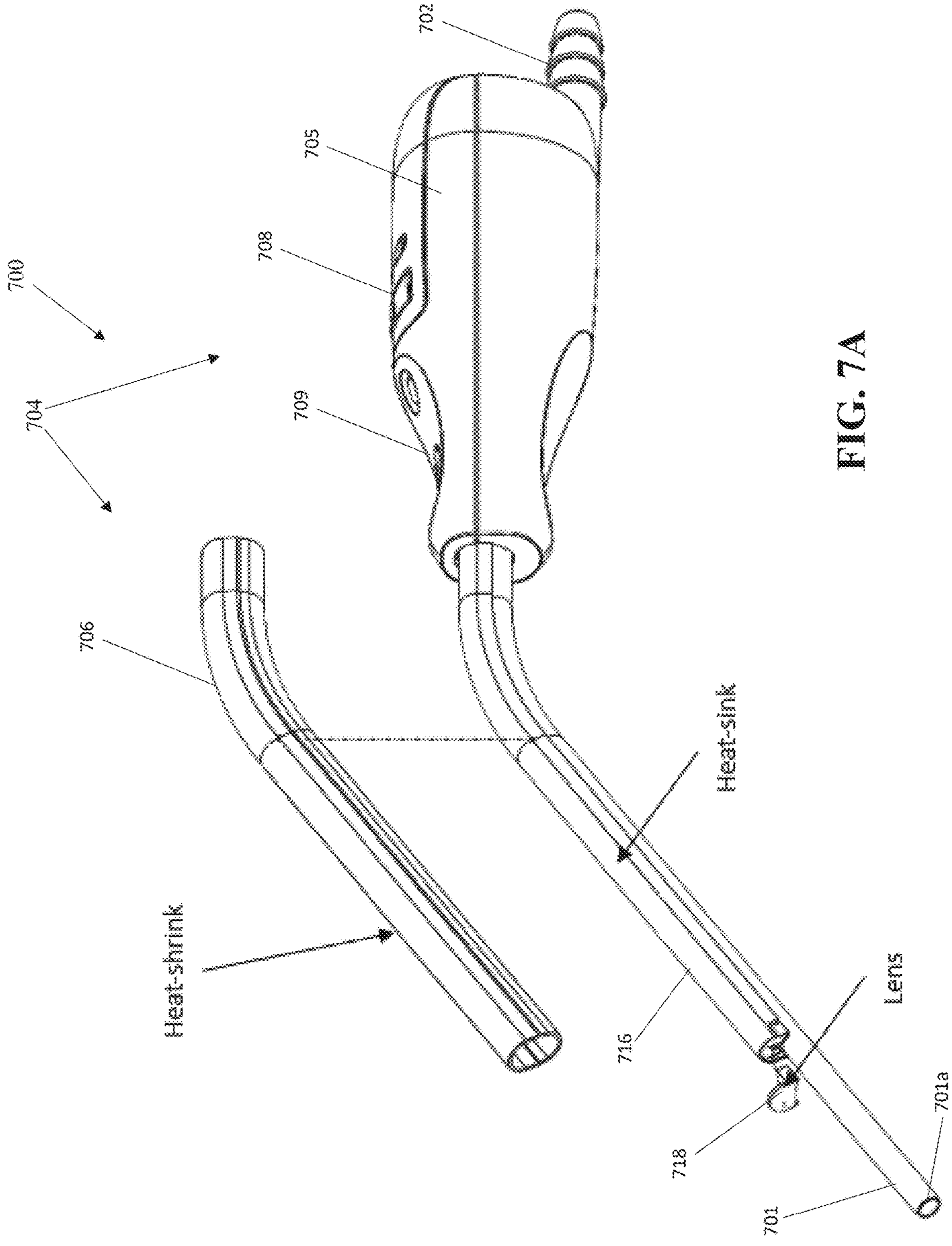
FIG. 7A shows another embodiment of the illuminated suction device of the present invention with a separately formed lens.
Figure 7B:
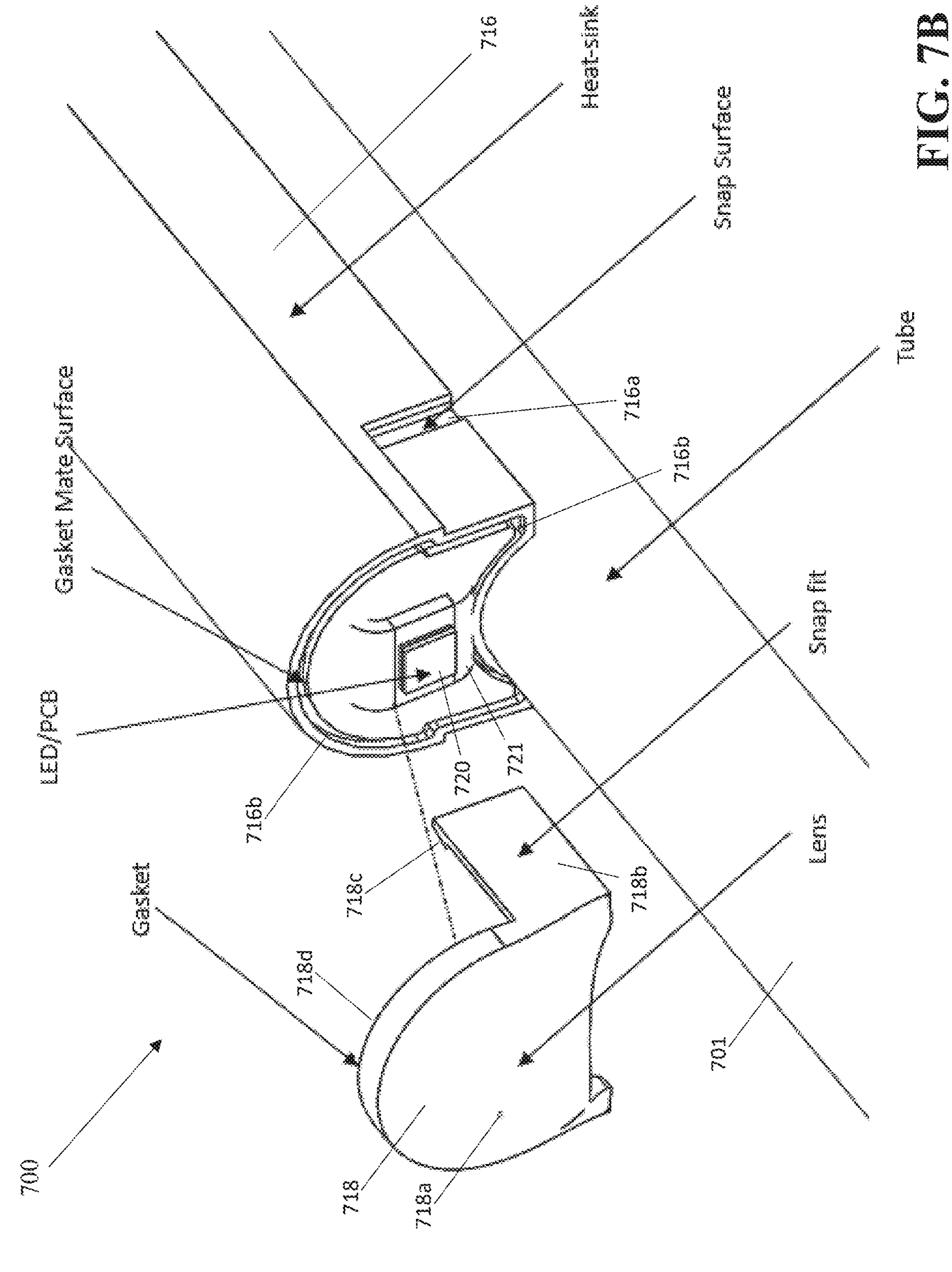
FIG. 7B shows an enlarged view of the illuminated suction device of FIG. 7A.

The suction device 100 of FIGS. 1A-1E also includes an outer housing 104 which forms an ergonomic handle 105 for holding and manipulating the device and an elongated outer housing portion 106 extending from the handle to cover a portion of the suction tube 101 and at least a portion of the illumination assembly. As shown in FIGS. 1A-1E, the elongated outer housing portion 106 covers and encloses most of the illumination assembly except for the distal end of a spine with a lens at its distal end. In certain embodiment, such as the embodiments shown in FIGS. 3A-4E, the lens is integrated into and is part of the spine. In other embodiments, the lens may be formed separately from the spine and may be attached to the distal end of the spine, such as by snap fitting or other suitable attachment. This allows the spine and the lens to be formed from different materials to provide different functionalities. One illustrative embodiment in which the lens is separately formed and is attached to the spine is shown in FIGS. 7A-7B described below.

In the illustrative embodiment of FIGS. 1A-1E, the handle 105 is formed from rigid materials, such as a rigid plastic or polymer material, and the elongated outer housing portion 106 is formed from a thin and flexible material. For example, the elongated outer housing portion 106 may be formed from a flexible polymer or plastic material, such as a heat shrink tubing material, that does not add a substantial thickness to the circumference of the device. The flexible housing 106 in the embodiments shown is opaque, but in other embodiments, the flexible housing may be translucent or transparent, depending on the positioning of the light source(s) and the desired illumination characteristics.

As shown, the handle 105 is formed from two portions, including an upper housing portion 105*a* and a lower housing portion 105*b*, which are held together to form an enclosure for internal components, including one or more power sources and electrical components of the illumination assembly, and to accommodate a controller 109 for controlling the illumination assembly and for suction through the suction tube. The upper and lower housing portions 105*a*, 105*b* may be attached together using ultrasonic welding, any suitable fasteners, such as screws, using glue or other adhesive materials or may be snap fit together or attached using any other shape coupling or interlocking methods, or a combination of any of these methods.

One of the upper and lower housing portions 105*a*, 105*b* includes a battery cover 107 that can be opened or removed for exposing one or more power sources housed within the handle 105. The battery cover 107 includes an opening therein for inserting a push-tab 108 of a push-tab assembly, which is used to control whether or not the illumination assembly can be turned ON using a controller by electrically disconnecting the power source(s) from circuitry of the illumination assembly in a "storage" configuration and by electrically connecting the power source(s) to the circuitry of the illumination assembly to close the circuit in a "use configuration." In FIG. 1A, the push-tab 108 is pushed into the opening of the battery cover 107 and into handle 105 and is in the "use" configuration, while in FIGS. 1B-1D, the push-tab 108 extends partially outside of the battery cover 108 and is in the "storage configuration." The push-tab assembly also assists in removing the one or more power sources from the handle 105 without requiring physical contact of the user with the one or more power sources by hooking around a portion of the one or more power sources, or otherwise physically engaging with the power source(s), when the one or more power sources are housed in the handle 105 and causing the one or more power sources to be removed from the handle 105 when the battery cover 107 is opened. The details of the push-tab 108 and of the push-tab assembly and how it interacts with the electrical components of the illumination assembly and the power source(s) are described in U.S. Pat. No. 10,512,519, assigned to the same assignee herein and incorporated herein by reference. In other embodiments, the push-tab may be replaced by a pull-tab inserted into the opening of the battery cover. In such embodiments, the pull-tab is positioned at least partially within the opening of the battery cover and the handle in the "storage" configuration so as to electrically isolate or disconnect the power source(s) from the circuitry of the illumination assembly, and is partially or completely extended from or pulled out of the handle via the opening in the battery cover into the "use" configuration so as to electrically connect the power source(s) with the circuitry. In some embodiments, the pull-tab may be fully detachable from the battery cover and the handle, while in other embodiments, the pull-tab may remain attached to the battery cover even when in the "use" configuration. In certain embodiments, a dielectric tab may be used as the pull-tab and may be fully removable for "use" configuration.

As can be seen in FIGS. 1A-1E, one of the upper and lower housing portions 105*a*, 105*b* accommodates therein control portions (operating members) of the controller 109 for controlling the amount of suction through the suction tube and/or for controlling the illumination assembly. It is understood that the suction control by the controller 109 is optional and may be present in certain devices, such as the Frazier-type suction device, or may be absent in other devices, such as the Yankauer-type suction device.

In the present illustrative embodiment, the upper housing portion 105*a* includes a concave recessed portion 105*a*1 in an area located proximate to the elongated flexible portion 106 of the outer housing. The concave recessed portion 105*a*1 may be configured to slope inwardly in a direction toward the elongated flexible portion 106 so that the handle gradually tapers in thickness. The control portions of the controller 109 are accommodated in the concave recessed portion 105*a*1 in order to allow an operator to easily and comfortably control suction through the suction tube and the illumination assembly using one hand and in some cases, using one finger by sliding the finger within the concave recessed portion 105*a*1. In the illustrative embodiment of FIGS. 1A-1E, the lower housing portion 105*b* also includes a similar concave recessed portion 105*b*1 in an area located proximate to the elongated flexible portion 106, wherein the concave recessed portions 105*a*1 and 105*b*1 are formed on opposing upper and lower surfaces of the handle 105. This configuration of the handle provides an ergonomic handle that allows for easy one-handed operation.

In other embodiments, the concave recessed portion in the lower housing portion 105*b* may be omitted. In yet other embodiments, the control portions of the controller 109 may be accommodated in the concave recessed portion 105*b*1 in the lower housing portion 105*b*, and the upper housing portion 105*a* may or may not include a similar concave recessed portion. In yet other embodiments, the control portions of the controller 109 may be accommodated in the handle closer to the distal end of the handle 105, i.e., closer to the barb 102 or port, instead of being closer to the proximal end of the handle 105.

As shown in FIGS. 1A-1C and 1E, the control portions of the controller 109 include an illumination control portion 109*a* for controlling the illumination assembly and a suction control portion 109*b* for controlling the amount of suction through the suction tube. In this illustrative embodiment, the illumination control portion 109*a* includes a push button that controls the ON/OFF state of the illumination assembly. In the illustrative embodiment of FIGS. 1A-1C and 1E, the push button is positioned within a recess in the concave recessed portion 105*a*1 so that the top surface of the button is slightly below or at the surface of the concave recessed portion 105*a*1 in order to prevent inadvertent activation/deactivation of the illumination assembly. However, in other embodiments, the illumination control portion 109*a* may include any other suitable control portion, including, but not limited to, a switch, a toggle, a potentiometer, a slide or a dimmer switch, any other mechanical switch, control mechanism or activation device for controlling the ON/OFF state of the illumination assembly and/or for controlling brightness, hue and other light characteristics of the illumination assembly and/or for controlling selection of light source(s) to be turned ON/OFF and to be adjusted in a case of an illumination assembly with multiple light sources.

The suction control portion 109*b* includes an elongated opening which can be covered fully or partially by a user's finger to control the amount of suction being provided through the suction tube and at the distal tip of the suction tube. The elongated opening is in fluid communication with a corresponding opening in the suction tube (not shown), and when a user covers the opening completely, full suction amount will be present at the distal tip of the suction tube. When a user partially covers the opening of the suction control portion 109*b*, the amount of suction at the distal tip of the suction tube can be controlled based on how much of the opening is covered by the user's finger.

Figure 1B:
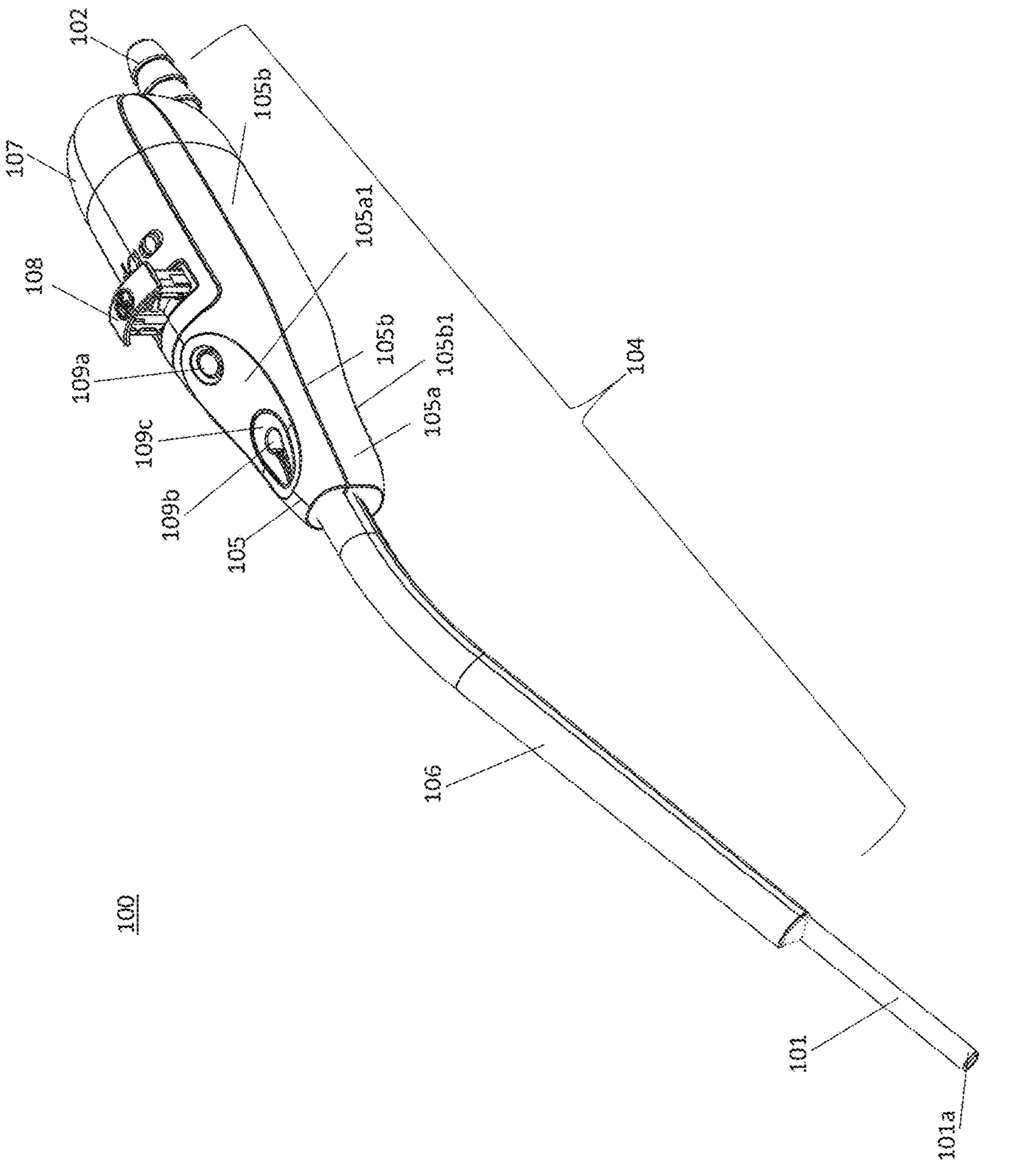
Figure 1C:
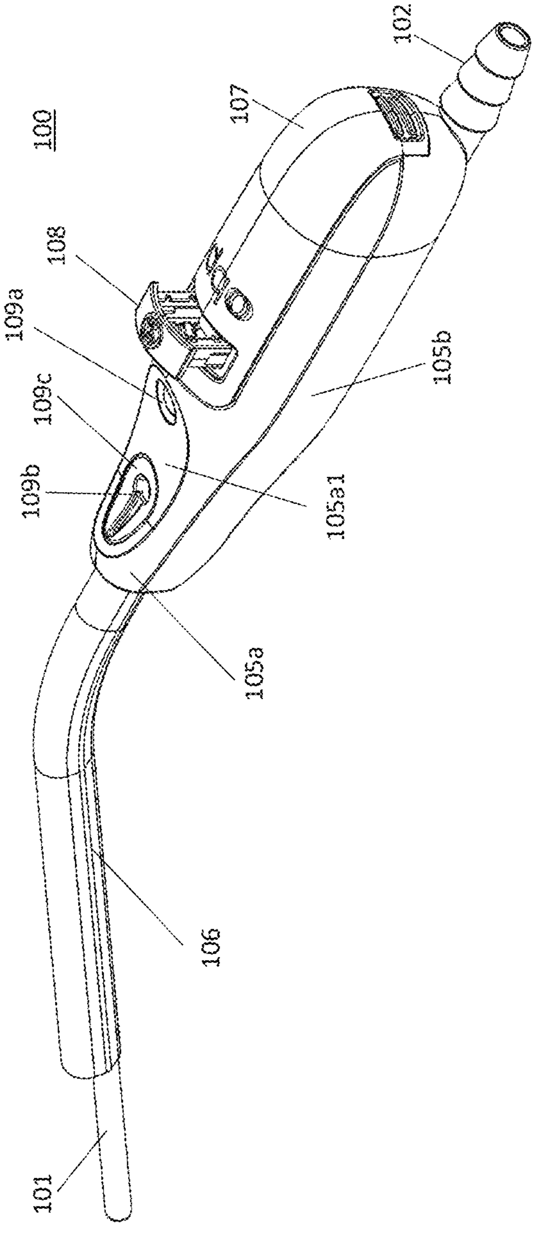
Figure 1D:
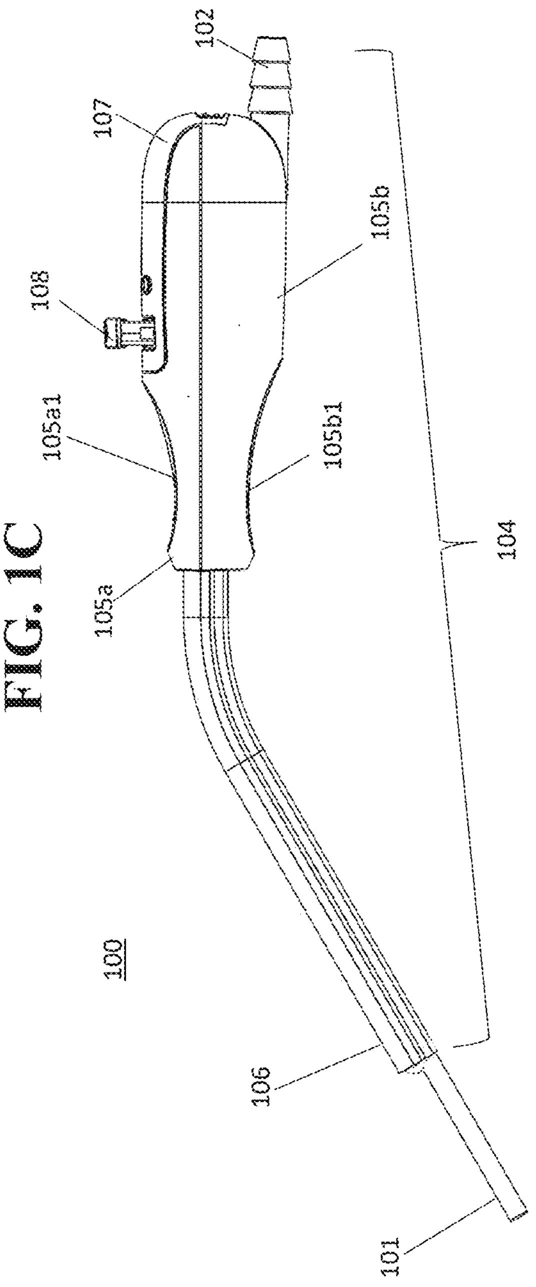
Figure 1E:
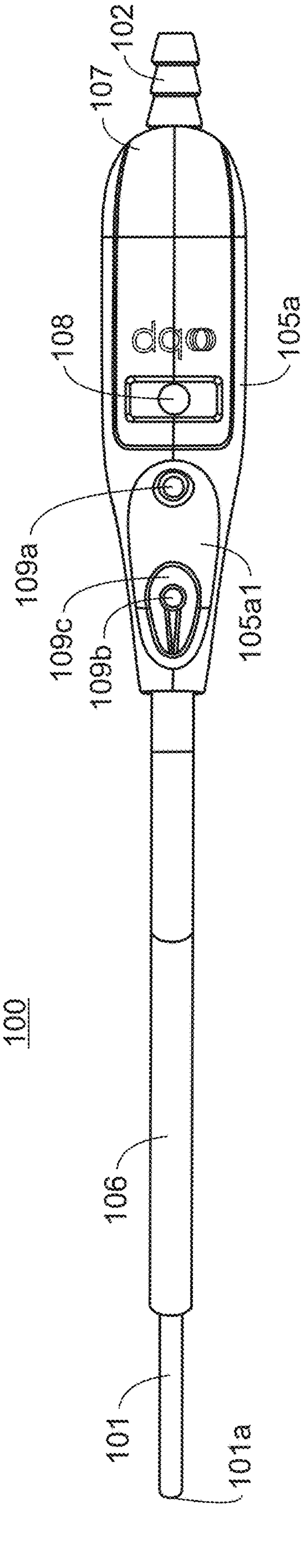

In order to provide for fine and precise control of the amount of suction at the distal tip of the suction tube, the opening in the suction control portion 109*b* has a generally elongated tear shape or key-hole shape that includes a wider portion and an elongated slit-like or narrower portion extending from the wider portion. In one example, the suction control portion 109*b* includes a wider, circular potion and an elongated slit portion extending from the circular portion and tapering, i.e., narrowing in width, in a direction away from the circular portion. In other embodiments, other shapes may be used for the wider portion and the elongated portion may or may not taper. The shape of the opening allows the user to cover the circular portion of the opening with a finger to provide an initial amount of suction and to slide the finger so as to cover the elongated slit portion as needed, in order to increase or decrease the amount of suction being provided to the distal tip of the suction tube. In addition, as shown in FIGS. 1A-C, the controller 109 forms a recessed oval, rounded or egg-shaped peripheral surface 109*c* around the periphery of the opening 109*b* for ergonomically accommodating the user's finger. This recessed peripheral surface 109*c* provides a tactile guide for the user's finger to the location of the opening 109*b* so that the user can find the opening 109*b* through touch without having to visually find the opening in the suction control portion 109*b*.

The elongated outer housing portion 106 encloses a portion of the suction tube 101 and optical and heat dissipation components of the illumination assembly described in more detail below. Specifically, the elongated outer housing portion 106 holds the optical and heat dissipation components of the illumination assembly against an external surface of the suction tube 101, and a distal end of the elongated outer housing portion 106 is open to expose a distal end of a lens so that light emitted from a light source is directed to a target area above and in front of the distal tip 101*a* of the suction tube.

Figure 2A:
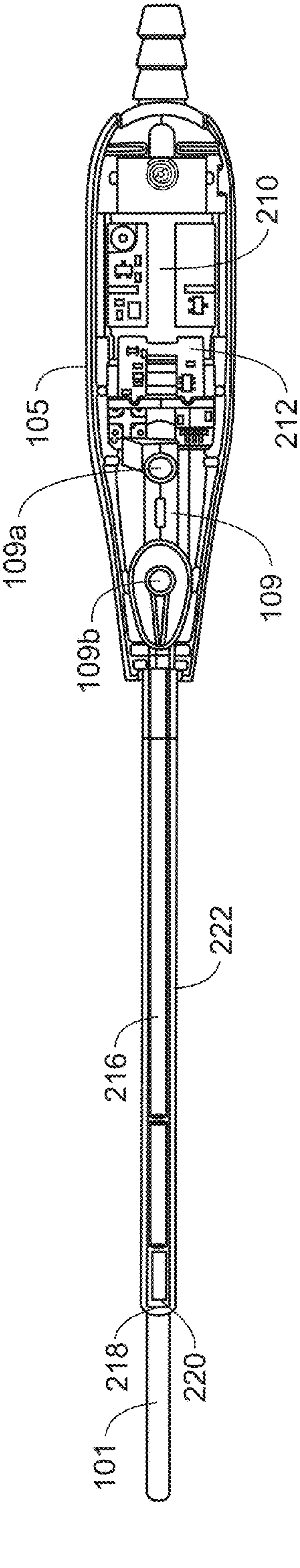
FIG. 2A shows a top view of the illuminated suction device of FIGS. 1A-1E with a portion of its outer housing removed to expose internal components.
Figure 2B:
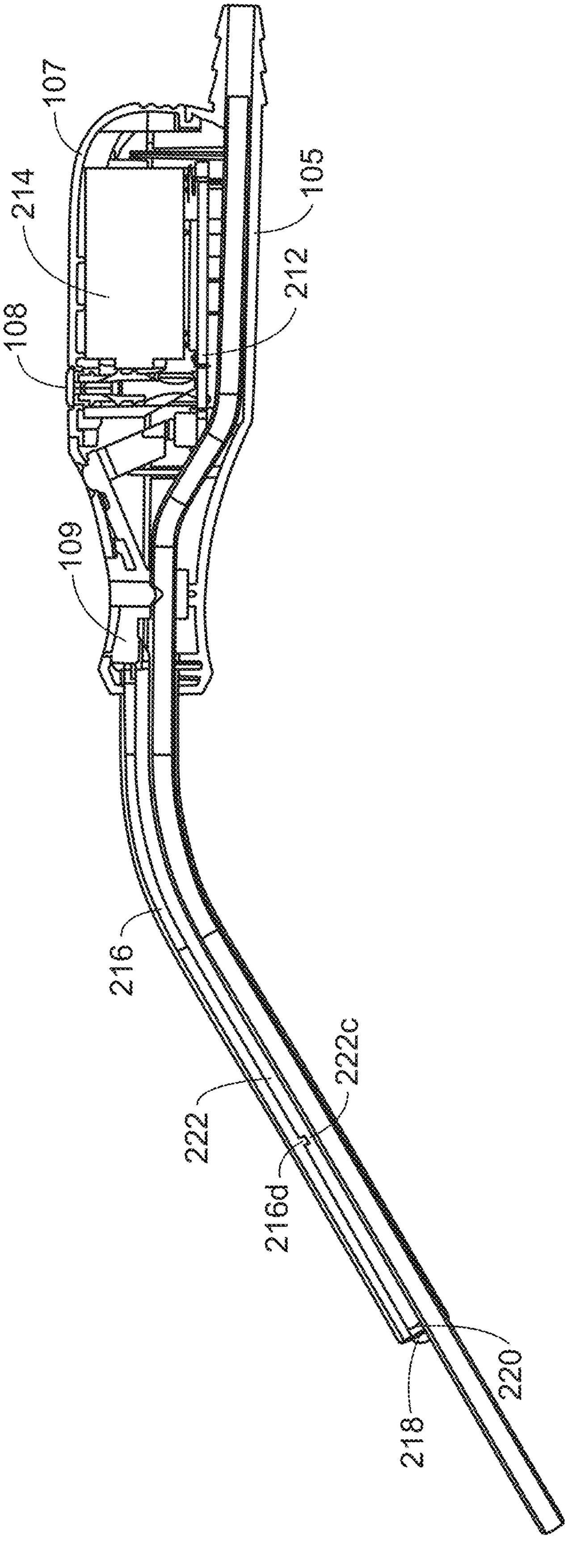
FIG. 2B shows a cross-sectional side view of the illuminated suction device of FIGS. 1A-1E.

FIG. 2A shows a top view of the suction device 100 with a top portion of the housing 104 and the power source(s) removed so as to expose internal components enclosed by the housing 104. FIG. 2B shows a side cross-sectional view of the suction device to demonstrate the internal components within the housing 104 of the suction device 100.

As shown in FIGS. 2A and 2B, the handle 105 of the housing 104 includes a chassis 210 therein for positioning and holding in place the internal components, including portions of the illumination assembly and the controller 109. In addition, the chassis 210, in combination with a power source housed within the handle 105, adds rigidity to the suction device. In some embodiments, the chassis 210 comprises a plurality of ribs or projections formed on the interior surface of the handle 105, while in other embodiments, the chassis 210 may be a separate component or frame for positioning the internal components within the handle 105. As can be seen in FIG. 2B, the suction tube 101 extends from the barb or port 102 formed at the distal end of the handle 105 through the length of the handle 105, through the elongated housing portion 106 and has an exposed distal end. The suction tube 101 is held in place by an overmold at one end of the handle 105 adjacent to the flexible housing 106 and by the suction port or barb 102 at the other end of the handle 105.

The portions of the illumination assembly housed within the handle 105 include a printed circuit board (PCB) assembly 212, such as a rigid PCB, for controlling one or more direct light sources of the illumination assembly, and at least one power source 214 for providing power to the illumination assembly. The PCB assembly 212 includes circuitry and switches for illumination assembly control as well as electrical connections for electrically connecting to the at least one power source 214. In some embodiments, the PCB assembly 212 includes one or more ON/OFF control circuits and switches for controlling the at least one light source. In other embodiments, the PCB assembly includes a dimmer circuit and/or one or more circuits for controlling the sequence of turning ON/OFF and/or the color and/or the brightness of the at least one light source, similar to the one described in U.S. Pat. No. 10,512,519, which is assigned to the same assignee herein and incorporated herein by reference.

In addition, as discussed above, the push-tab 108 is inserted into the handle through an opening in the battery cover to electrically isolate the at least one power source in one position and to electrically connect the at least power source in another position. As shown in FIG. 2B and as described in more detail below, the controller 109 is overmolded onto the suction tube 101 and positioned within the handle 105 relative to the suction tube so that the opening in the suction control portion 109*b* of the controller 109 is in fluid communication with a corresponding opening in the suction tube, and also positioned relative to the PCB assembly 212 so that the illumination control portion 109*a* is in communication with illumination control switch(es) on the PCB assembly 212.

As shown in FIGS. 2A and 2B, the elongated housing portion 106 encloses or partially encloses the at least one light source 220, the optical components and the heat dissipation components of the illumination assembly, as well as electrical connections between the at least one light source and the PCB assembly 212. As described in more detail below with respect to FIGS. 3A-5B, the optical components include a spine 216 extending along a majority of the length of the elongated housing portion 106 and one or more lenses 218 integrated into the spine 216. In the illustrative embodiment of FIGS. 2A-2B, the spine 216 extends along the entire length or substantially the entire length of the elongated housing portion 106 and has an integrated lens 218 formed at its distal end which is exposed through an opening in the elongated housing 206. As mentioned above, in some embodiments the lens 218 is formed separately from the spine 216 and is attached to the spine, wherein the attachment may be removable or non-removable. Moreover, as mentioned above, the illumination assembly does not use a waveguide or a lightguide and thus, loss of brightness from the light source is minimized.

The heat dissipation components of the illumination assembly include at least one heat dissipation member or heat sink 222 for dissipating heat generated by the at least one light source 220. As described in more detail below and as shown in FIGS. 3A-3C and 5A-5B, the heat sink extends from the light source 220 along the suction tube 101 and along the spine 216 in a direction away from the distal end of the suction tube and toward the handle 205. In certain embodiments, the heat sink 222 extends along a portion of the length of the spine 216 and in some embodiments, the heat sink 222 extends along a majority portion of the length or along the entire length of the spine 216. As described in more detail below with respect to FIGS. 7A-7B, the spine and the heat sink may be combined into a single component so that the heat sink forms the spine and has a lens attached thereto.

Figure 3A:
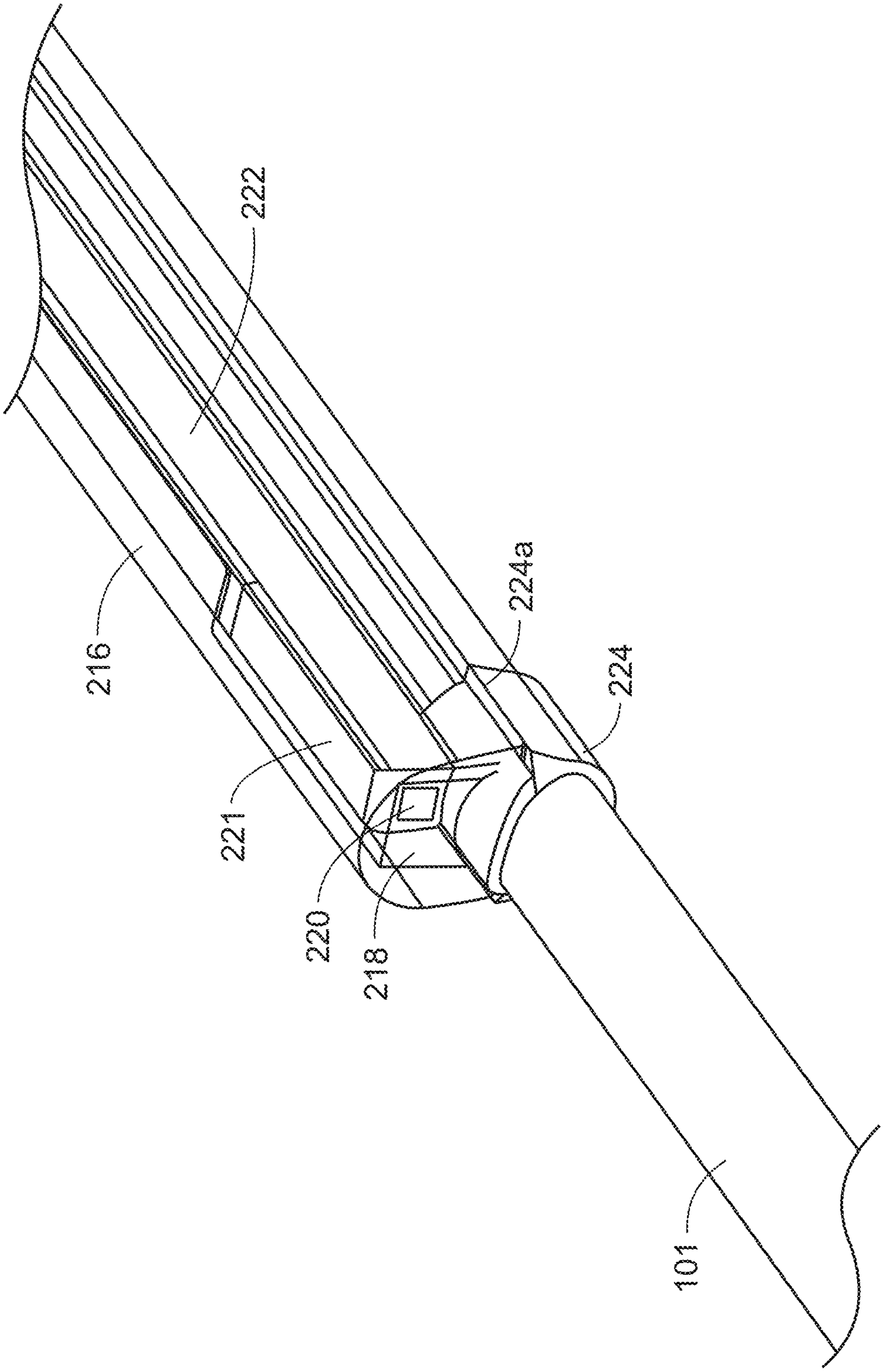
FIG. 3A shows a close-up view of a portion of the illumination assembly with the outer housing removed to expose internal components.
Figure 3B:
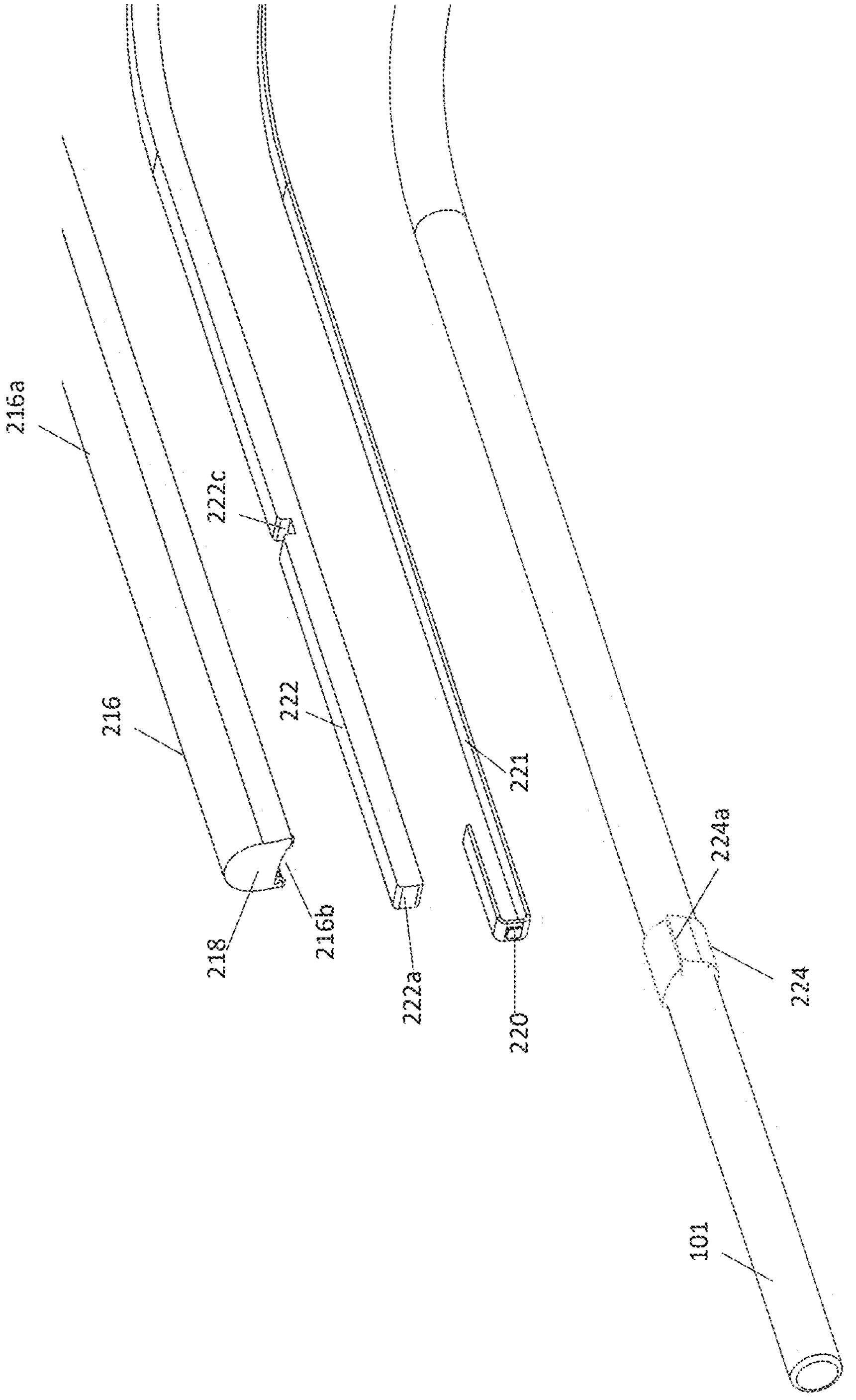
FIG. 3B shows an exploded view of the portion of the illumination assembly of FIG. 3A.
Figure 3C:
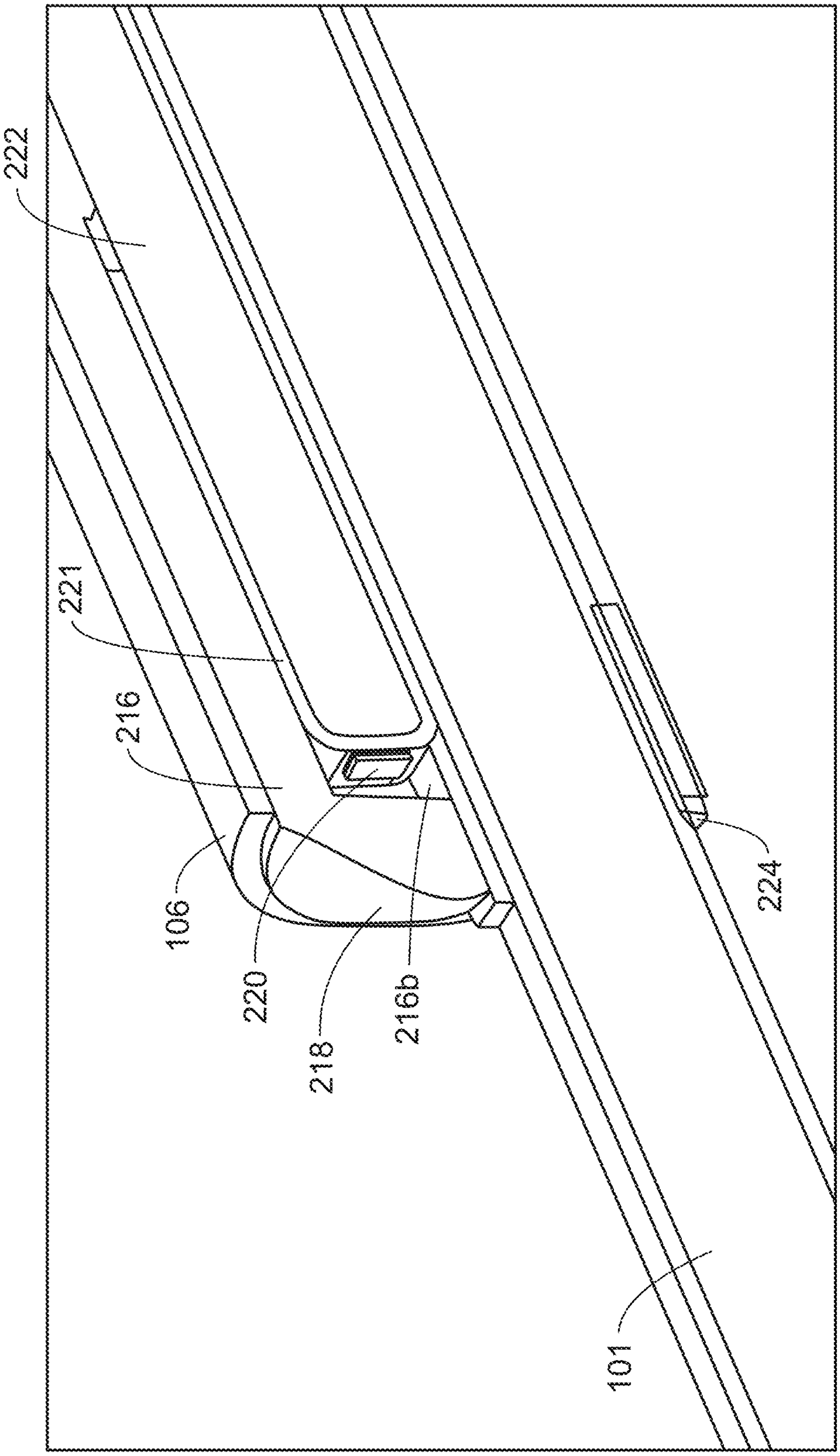
FIG. 3C shows a cutaway view of the portion of the illumination assembly to expose internal components.

FIGS. 3A-3C show in more detail the configuration and assembly of the illumination assembly components together with the suction tube 101 to provide a compact, low-profile assembly in a limited available space that does not block the view of a user when using the suction device. Specifically, FIG. 3A shows a more detailed assembled view with the elongated housing removed and FIG. 3B shows an exploded view of the illumination assembly components and suction tube. FIG. 3C shows a cut-away view of the illumination assembly components and the suction tube.

As shown in FIGS. 3A-3C, the illumination assembly components include the at least one light source 220 mounted on a flexible circuit 221, such as a flexible PCB, the heat sink 222, and the spine 216 with the integrated lens 218. Although in the present illustrative embodiment the flexible PCB is used for mounting the one or more light sources 220 thereon, in other embodiments, the at least one light source 220 may instead be mounted on a rigid circuit board or may be connected to a rigid circuit board using wires, while in yet other embodiments, the at least one light source 220 may be connected to the PCB assembly 212 using wires. Furthermore, in some illustrative embodiments, the heat sink 222 may be electrically active, such as by being electrically connected to the one or more power sources, so that the heat sink 222 is capable of powering the one or more light sources 220. In such embodiments, the need for a flexible or rigid circuit board may be eliminated.

The suction tube 101 has a gasket 224 provided thereon for positioning the illumination assembly components relative to the outer surface of the suction tube 101 and sealing any gaps between the suction tube 101, the illumination assembly components and the opening in the distal end of the elongated housing 106. In the embodiment shown in FIG. 3B, the gasket 224 extends around the circumference of the suction tube 101 at a position adjacent a distal end of the illumination assembly, has rounded top and bottom surfaces and projection 224*a* on each side of the gasket 224 which create cradling surfaces for positioning and sealing the illumination assembly with the suction tube. Gasket 224 may also be integrated into the spine 216 using over molding or other method, or may be integrally formed with the spine 216.

Figure 4A:
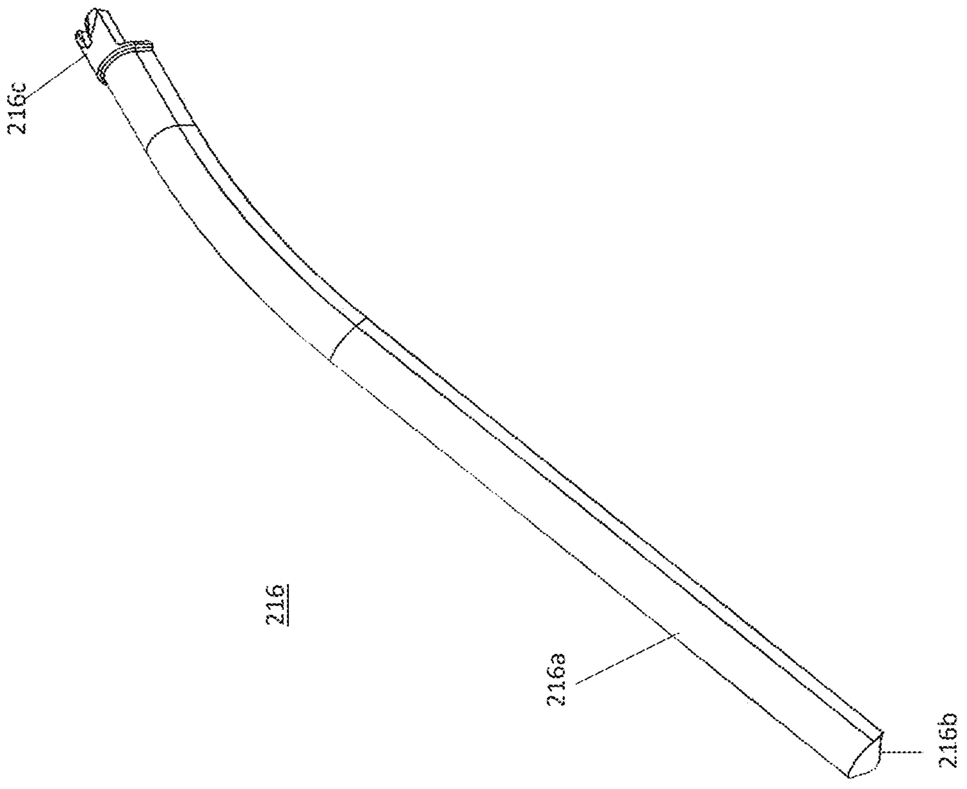
FIG. 4A shows a spine with an integrated lens of the illumination assembly of FIGS. 3A-3B.
Figure 4B:
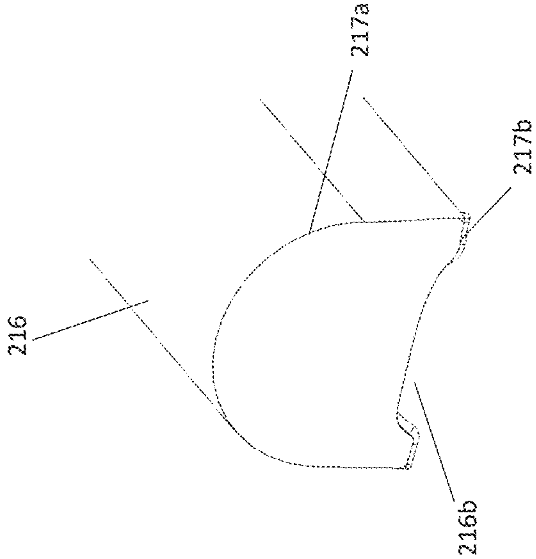
FIGS. 4B-4E show different views of the spine portion with the integrated lens.
Figure 4C:
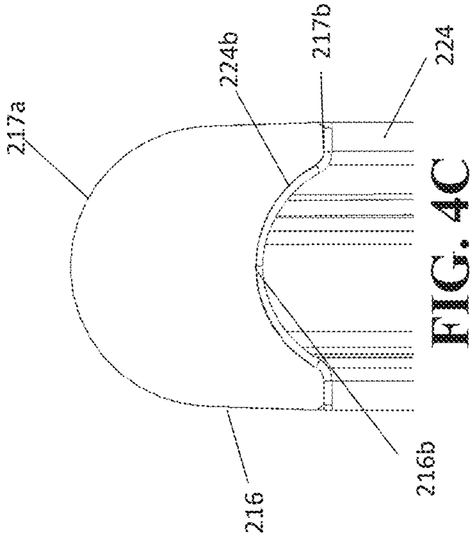
Figure 4E:
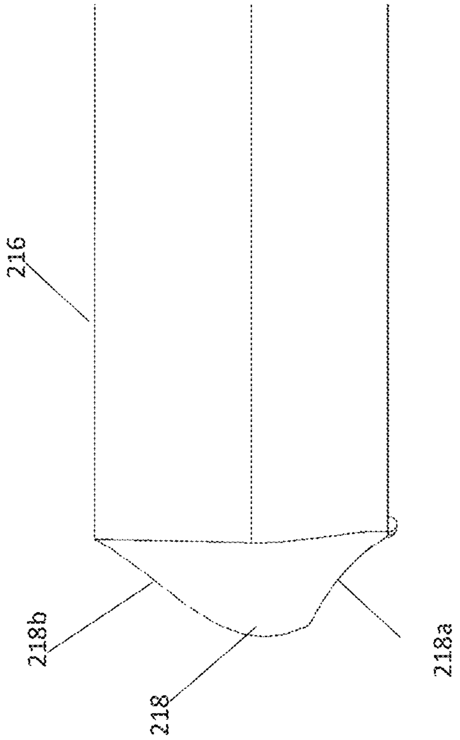
Figure 4D:
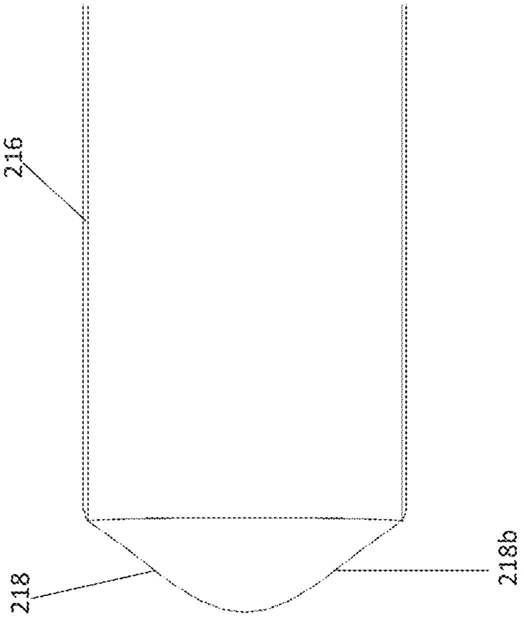
Figure 5A:
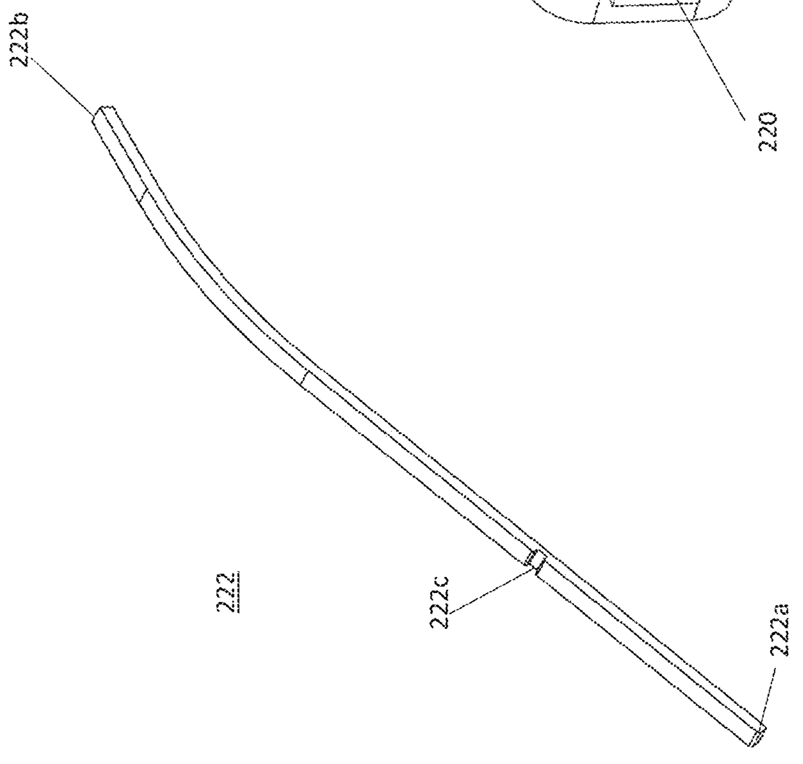
FIG. 5A shows a heat sink member of the illumination assembly of FIGS. 3A-3B.
Figure 5B:
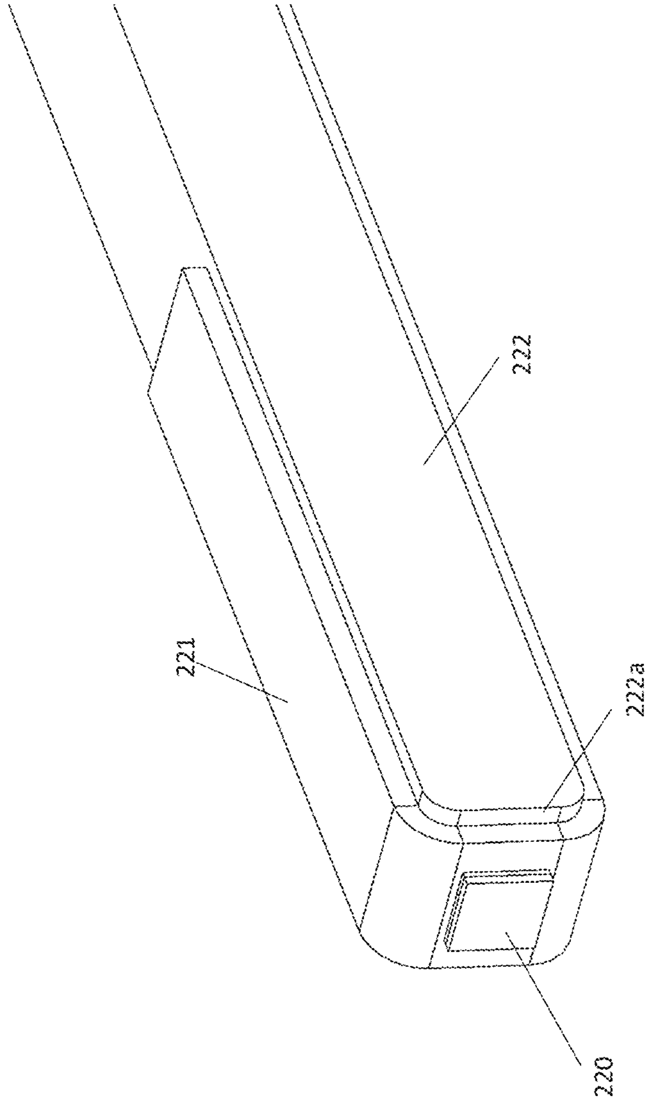
FIG. 5B shows a portion of the heat sink member assembled with a light source.

The components of the illumination assembly are shown individually in more detail in FIGS. 4A-5B. FIGS. 4A-4E show in more detail the configuration of the spine 216 and the integrated lens 218. FIG. 5A shows in more detail the heat sink 222 and FIG. 5B shows in more detail the assembly of the heat sink 222 with the flexible circuit 221 and the light source 220 mounted thereon.

In the embodiment of FIGS. 3A-3C and 5A-5B, the heat sink 222 comprises a rod-shaped elongated member having a distal end 222*a* and a proximal end 222*b*. The heat sink 222 is formed from heat conducting material, which may be metallic. Exemplary materials for the heat sink include aluminum, copper and/or stainless-steel metals, and alloys thereof, ceramic materials, or other suitable heat conductors. Although not shown in FIGS. 3A-3C and 5A-5B, the heat sink 222 in the present illustrative embodiment extends from the handle 105 at its proximal end 222*b* along a portion of the length of the suction tube 101 to a location offset from the suction tube's distal tip. The proximal end 222*b* of the heat sink may be positioned at the distal or proximal end of the handle 105 or may overlap with the handle. As shown in FIGS. 5A-5B, the illustrative heat sink 222 has a square or rectangular cross-section for ease of assembly with the other components. However, in other variations, the cross-section of the heat sink may vary depending on the configuration and shape of the other components.

In the present illustrative embodiment shown in FIGS. 3A-3C and 5B, the light source 220 is mounted on the flexible circuit 221 by soldering the light source 220 onto a flexible circuit substrate or using other suitable techniques. The position of the light source 220 on the flexible circuit 221 is spaced away, or offset, from an end of the flexible circuit substrate so that there is sufficient length of the flexible circuit substrate on each side of the light source 220 to wrap around the heat sink 222, and in particular, around the distal end 222*a* of the heat sink 222. The flexible circuit 221 also includes electrical connections from the light source 220 to a connection end (not visible) of the flexible circuit 221, which electrically connects to the PCB assembly 212. As shown in FIGS. 3A and 5B, the flexible circuit 221 with the light source 220 mounted thereon is wrapped around a distal end 222*a* of the heat sink 222 so that the light source 220 is positioned at the flat or substantially flat end of the heat sink and so that the light source 220 emits light toward the distal end 101*a* of the suction tube 101 during operation. The flexible circuit 221 is attached to the heat sink 222 using an adhesive, such as pressure sensitive adhesive or an adhesive backing, or using any other suitable methods.

As can be seen in FIGS. 3A-3C and 5B, a shorter free end of the flexible circuit 221 extends along a portion of the upper surface of the heat sink 222, while a longer opposing end of the flexible circuit 221 with the electrical connection to the PCB assembly 212 extends along the lower surface of the heat sink 222. However, in other embodiments, the free end of the flexible circuit 221 may extend along the lower surface of the heat sink 222 while the other end of the flexible circuit with the electrical connection to the PCB assembly 212 extends along the upper surface of the heat sink 222. In yet other embodiments, the flexible circuit 221 may be wrapped around the distal end 222*a* of the heat sink 222 so that the ends of the flexible circuit extend along respective side surfaces of the heat sink 222. The positioning of the flexible circuit 221 around the distal end 222*a* of the heat sink 222 is dependent on the positioning of the PCB assembly 212 within the handle 105 and is selected for ease of electrical connection to the PCB assembly 212.

It is understood that in some embodiments, multiple light sources may be mounted on the flexible circuit 221 so as to provide brighter illumination or additional illumination in different positions. In such embodiments, the light sources may be mounted side by side on the flexible circuit 221 so that they are positioned at the flat distal end 222*a* of the heat sink 222 when the flexible circuit 221 is wrapped around the heat sink end. In some embodiments, the light sources may be mounted at different positions on the flexible circuit 221 along its length, such that illumination is directed at different angles relative to the suction tube. For example, in some embodiments, additional light source(s) may be provided on the flexible circuit portion that extends along the upper surface of the heat sink 222, and in some embodiments, additional light source(s) may be provided on one flexible circuit portion or on both flexible circuit portions extending along the side surfaces of the heat sink 222. With the arrangement shown in FIGS. 3A-3C and 5B, as well as the alternative arrangements using multiple light sources, heat generated by the one or more light sources 220 is absorbed by the heat sink 222 during operation, which allows the light source(s) 220 to operate at higher brightness for longer periods of time without causing tissue damage and without causing discomfort to the user's hand. In addition, by wrapping the flexible circuit 221 around the distal end of the heat sink 222, a compact, low-profile structure is achieved that is capable of retaining the positioning of the light source(s) 220 relative to the suction tube 101 and relative to the heat sink 222 without a substantial increase in the circumference of the suction tube and without interference with the viewing area of the user.

As shown in FIGS. 3A-3C and 4A-4B, the spine 216 comprises an elongated member 216*a* with a channel 216*b* extending along its length that opens in a direction facing the suction tube. When assembled with the heat sink 222 and the flexible circuit 221 with the at least one light source 220 mounted thereon, the spine 216 is positioned adjacent a portion of the suction tube 101 so that the heat sink 222 and the flexible circuit 221 with the light source(s) 220 thereon are fitted within the channel 216*b* in the spine 216, and are enclosed between the spine 216 and the suction tube 101. In certain embodiments, the channel 216*b* is shaped so as to correspond in shape to the assembled heat sink 222 with the flexible circuit 221 and light source 220 mounted thereon. This configuration is best visible in FIGS. 3A and 3C. For example, as can be seen in FIGS. 3A and 3C, in the present illustrative embodiment, the channel 216*b* accommodates the height and width of the heat sink 222 with the flexible circuit 221 and the light source 220 near a distal end of the spine 216, and decreases in height after a predetermined distance away from the distal end of the spine 216 to correspond to the reduced height of the heat sink 222 without the flexible circuit 221 adjacent thereto. In addition, as can be seen in FIG. 5A, the heat sink 222 may include a positioning recess 222*c* on its surface that faces the spine 216 when assembled, and as can be seen in FIG. 2B, the spine 216 may include a corresponding projection 216*d* within the channel 216*b* that is positioned so as to engage with, or fit into, the recess 222*c* in the heat sink 222. Alternatively, the heat sink 222 may include a projection on its surface and the spine 216 may include a corresponding recess positioned to engage with the projection on the heat sink. These configurations secure the positioning the spine 216 relative to the heat sink 222 to prevent shifting. In some embodiments, multiple positioning recesses and corresponding projections may be included in the heat sink 222 and the spine 216, with each recess being provided on one of the heat sink and the spine and the corresponding projection being provided on the other of the heat sink and the spine.

In the present illustrative embodiment, the elongated member 216*a* of the spine 216 is formed from a transparent and/or translucent material, such as a transparent or translucent plastic or polymer material, and is positioned along a portion of the suction tube 101 so that its distal end is spaced away from the distal end of the suction tube 101 and its proximal end is inserted into the handle 105 and overlaps with the handle 105 for a predetermined distance. In certain embodiments, the spine 216 is formed from other materials, which, in some embodiments, are non-electrically conductive materials and are poor conductors of heat. As shown in FIG. 4A, a proximal end of the spine 216 includes a connector 216*c* configured to connect with internal components of the handle 105 so as to secure the spine 216 to the handle 105 and relative to the suction tube 101.

As mentioned above, the spine 216 integrates therein a lens 218 for refracting light emitted from the light source 220 and focusing the light from the light source 220 to a predetermined target area. The lens 218 can also be a separate component that is not integrated into the spine 216 allowing for the use of differing materials between the lens 218 and the spine 216. In the present illustrative embodiment, the lens 218 is integrated into the distal end of the spine 216 so as to refract light emitted from the light source 220 positioned adjacent the distal end of the heat sink 222. FIGS. 4B-4E show an exemplary configuration of the lens 218 integrated into the spine 216 in more detail.

FIG. 4B shows an isometric view of the distal end of the spine 216 and FIG. 4C shows a front view of the distal end of the spine 216 with an abutting gasket 224 which seals space(s) formed between the spine 216 and the suction tube 101. As can be seen in FIGS. 4A and 4B, the spine 216 has a rounded top or outer surface 217*a* and a flattened bottom surface 217*b* with the channel 216*b* formed therein. The channel 216*b* adjacent the distal end of the spine 216 and adjacent the integrated lens 218 has a first, smaller depth as shown in FIGS. 3A-3B, and the gasket 224 has a top surface 224*b* that conforms to the shape of this channel 216*b* portion. Although not visible in FIGS. 4A-4C, the channel 216*b* in the spine 216 increases to a second, larger depth after the integrated lens 218 in order to accommodate the heat sink with the flexible circuit and the light source. This change in the channel 216*b* depth is visible in FIG. 3C.

It is understood that the shape of the spine 216 may be varied, depending on the configuration of the suction device, and in some embodiments, the top surface of the spine 216 may be square-shaped or pointed. However, in the present illustrative configuration, the rounded shape of the top surface 217*a* of the spine 216 facilitates the compact assembly that minimizes the risk of potential interference with or damage to the incision and surrounding tissues.

FIGS. 4D and 4E show top and right-side views, respectively, of the distal end of the spine 216 and show the shape of the lens in more detail. As shown in FIGS. 4D and 4E, the integrated lens 218 of the illustrative embodiment is an aspherical convex lens which has a convex surface formed at the distal end of the spine 216. In certain embodiments, the outer convex surface of the integrated lens 218 protrudes from the distal end of the spine 216 and from the outer housing that covers the spine, as can be seen in FIGS. 1A, 1B, 1D and 2B. In other embodiments, the lens 218 is fully enclosed by the spine 216 so that the spine forms a transparent or translucent outer surface distally in front of the lens 218. The lens 218 may be a convex lens, i.e., a double convex, or a biconvex lens, in some embodiments, while in other embodiments, the lens 218 may be a plano-convex lens with a convex outer surface and a planar inner surface that faces the light source. The lens radii and focal length are selected based on one or more of the desired light characteristics at the target site to be illuminated and the distance from the lens 218 to the distal tip of the suction tube and to the target site.

In the illustrative embodiment of FIGS. 4D and 4E, the lens 218 has a rounded or convex central region and aspheric surfaces in the peripheral regions of the lens. Specifically, as can be seen from FIGS. 4D and 4E, a peripheral region of the lens positioned adjacent to the suction tube 101 has a first aspheric surface 218*a* that is slightly concave, while the peripheral regions of the lens positioned further away from the suction tube 101 has slightly convex or planar aspheric surfaces 218*b*. The characteristics of the lens may be varied, however, based on the positioning of the lens along the length of the suction tube, the curvature of the suction tube and the distance of the lens from the desired target site.

The lens design can be customized to target a specific angle, shape, spread, color and intensity.

Figure 6A:
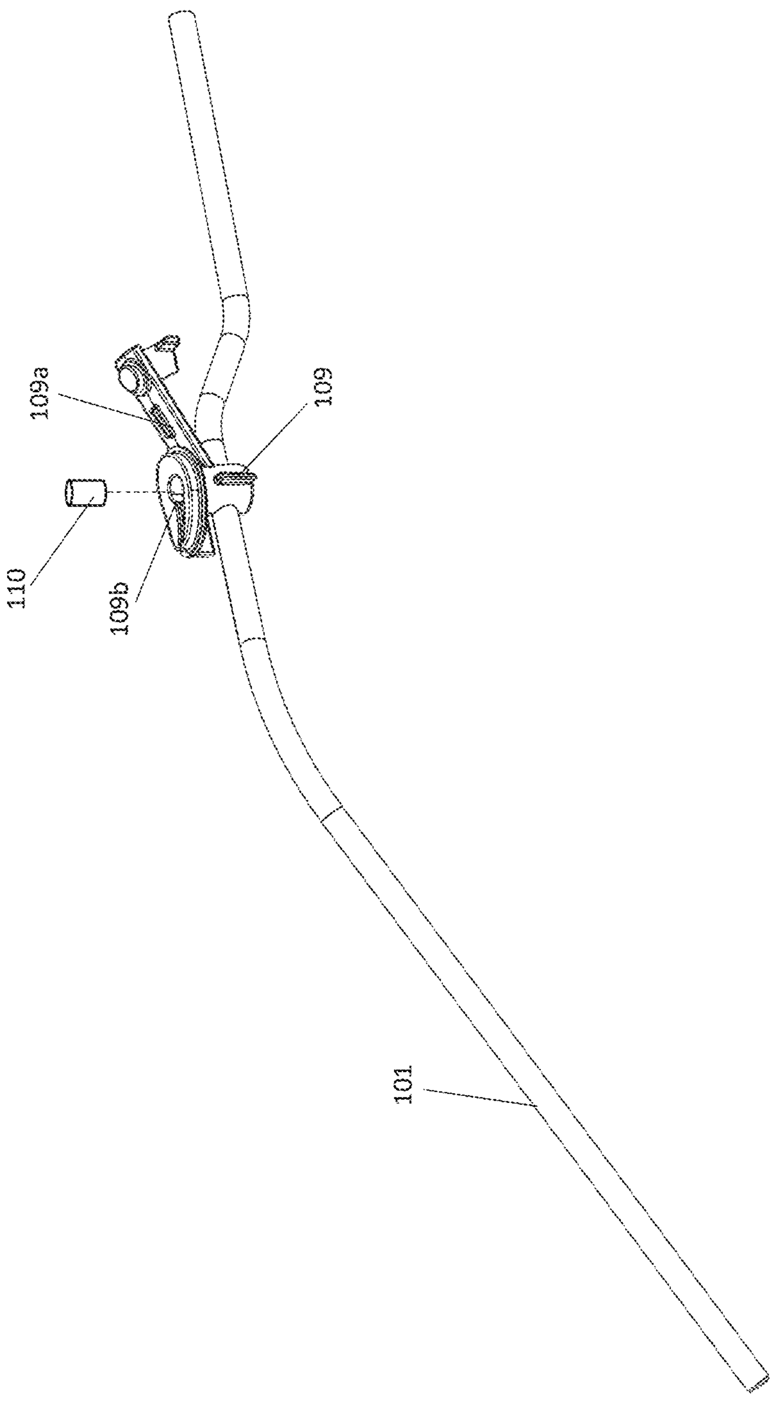
FIG. 6A shows a controller assembled with a suction tube of the suction device.
Figure 6C:
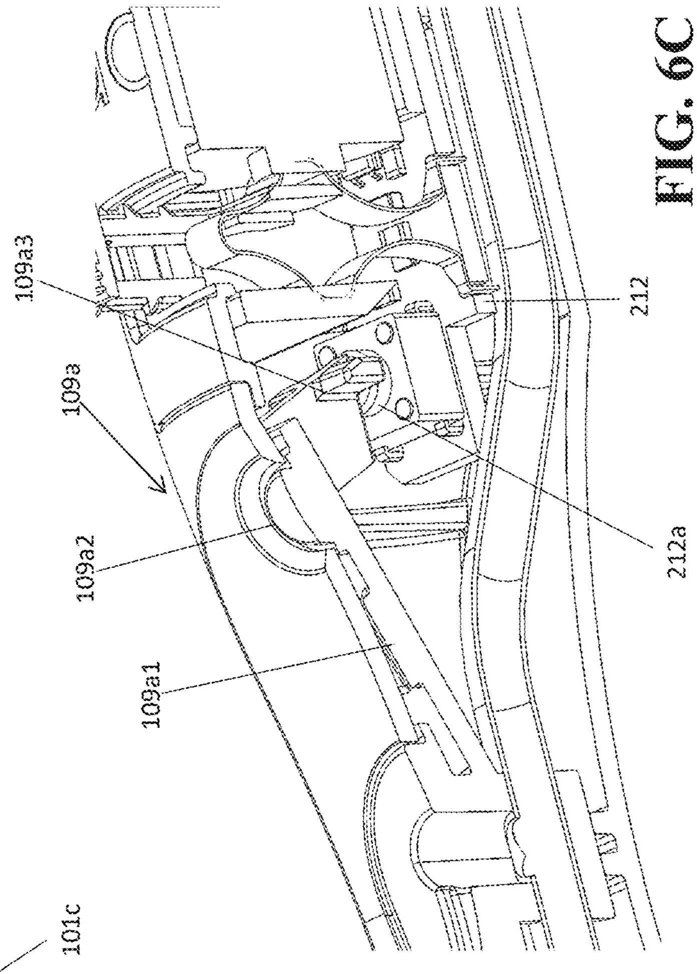
FIGS. 6B and 6C show cross-sectional views of the controller assembled with the suction tube and the outer housing of the suction device.
Figure 6B:
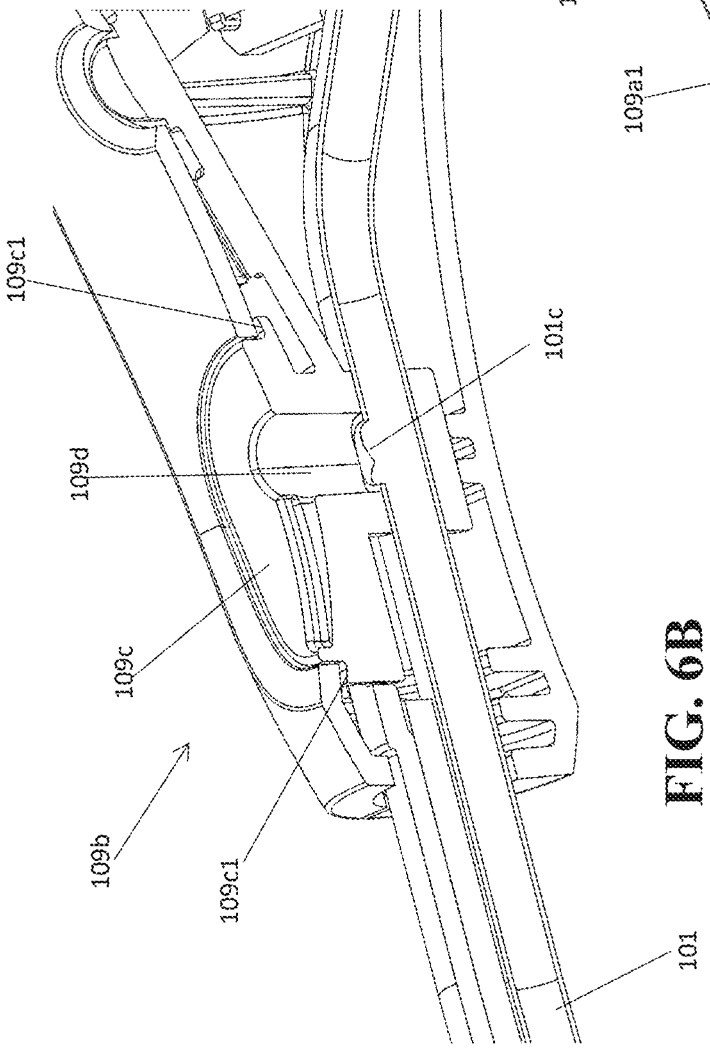

FIGS. 6A-6C show the illustrative controller 109 of the suction device for suction control through the suction tube 101 and for controlling the operation of the illumination assembly. FIG. 6A shows the controller 109 comprising the suction control portion 109*b* which is engaged with the suction tube 101 and the illumination control portion 109*a* extending from the suction control portion 109*b* and including at least one operation member or activation device. As discussed above with respect to FIGS. 1A-1E, the operation member or activation device in the present illustrative embodiment includes a push button, but in other embodiments, other activation and illumination control devices may be used.

The controller 109 in FIG. 6A is disassembled from the handle 105 of the suction device, which is not shown. In the illustrative embodiment shown, the controller 109 is overmolded onto, and around the circumference of, the suction tube 101 so that the opening in the suction control portion 109*b* is positioned so as to be in fluid communication with the opening in the suction tube 101. The attachment of the controller 109 to the suction tube 101 or the positioning of the controller 109 relative to the suction tube may be achieved using other methods, including using internal structures within the handle 105, i.e., chassis 210, and/or external structures on the suction tube 101 to position the controller 109 relative to the suction tube 101, or using fasteners such as clamps, adhesives, etc., or other suitable mechanisms. In the present illustrative embodiment, the controller 109 is integrally formed from plastic or other suitable polymer materials. In other embodiments, the controller 109 may be formed from multiple interconnected or fastened pieces.

FIGS. 6B and 6C show more detailed cross-sectional views of the controller 109 of FIG. 6A with a portion of the suction tube 101 and incorporated into the handle 105 of the suction device with a portion of the handle 105 visible in these views. FIG. 6B shows the suction control portion 109*b* of the controller 109 in more detail. As can be seen in FIG. 6B, the suction tube 101 includes a through opening 101*c* formed therein and the suction control portion 109*b* of the controller 109 includes a tear-shaped or keyhole-shaped opening 109*d* which is in fluid communication with, and at least partially overlaps with, the opening 101*c* in the suction tube 101. In the illustrative embodiment shown, the opening 109*d* includes a wider portion, which is aligned with and overlaps with the opening 101*c* in the suction tube 101 and a narrower elongated portion extending from the wider portion. In addition, as can be seen in FIG. 6B, the opening 109*d* is surrounded on all sides by an oval or egg-shaped peripheral portion 109*c*, which has a slightly concave exterior surface. As discussed above with respect to FIGS. 1A-1E, the peripheral portion 109*c* and its shape provide tactile stimulation or guidance to the user for easily finding the opening 109*d* and for easy tactile control of the suction by moving the user's finger over the opening 109*d*. As also discussed above, the configuration of the tear-shaped or keyhole-shaped opening 109*d* allows for finer suction control, whereby a user's finger can activate suction through the suction tube 101 by placing the finger over the wider portion of the opening 109*d* and moving the finger to cover a portion or all of the length of the elongated portion of the opening 109*d* so as to control the amount, or strength, of suction through the suction tube 101. The specific shape of the opening 109*d* is not limited to the shape shown in FIGS. 6A-6C and may be modified so as to provide adjustable suction control.

As can be seen in FIG. 6B, the suction control portion 109*b*, and in particular, the peripheral portion 109*c* thereof, is positioned within an opening in the concave recessed portion 105*a*1 of the handle. The concave outer surface of the peripheral portion 109*c* may be aligned or substantially continuous with the curvature of the outer surface of the concave recessed portion 105*a*1, or may be slightly more concave so as to provide additional tactile guidance for the user. The suction control portion 109*b* overmolded on the suction tube 101 may be held within the handle by the chassis within the handle, such as by one or more internal ribs or projections on the inner surface of the handle. For example, as shown in FIG. 6B, the inner surface of the lower housing portion 105*b* of the handle includes two projections thereon that abut the surface of the suction control portion 109*b* extending around the suction tube in order to maintain the position of the controller 109 relative to the handle 105. Similar internal projections are formed on the inner surface of the lower housing portion 105*b* adjacent the proximal end of the handle 105 to abut a lower surface of the suction tube 101 and to maintain the position of the suction tube 101 between the upper and lower housing portions 105*a*, 105*b*. Other internal projections or ribs on the inner surfaces of the upper and lower housing portions 105*a*, 105*b* are provided for maintaining the positioning of the controller 109, the suction tube 101 and other portions of the suction device, including portions of the illumination assembly overlapping with and extending into the handle 105.

In some embodiments, the suction control portion 109*b* is incorporated and positioned within the handle and is configured to seal or partially seal the opening in the concave recessed portion 105*a*1. As can be seen in FIG. 6B, the suction control portion 109*b* includes a lip 109*c*1 around the outer edge of the peripheral portion 109*c* which overlaps with the wall of the concave recessed portion 105*a*1 inside the handle 105. This provides sealing around the edge of the peripheral portion 109*c* of the suction control portion 109*b* so as to minimize air and fluid leaks.

As mentioned herein above, suction control may be optional or may be eliminated from the controller 109 depending on the type of the device with which the controller 109 is used. For example, in Yankauer-type suction devices, suction control is not required and thus, in such devices, the controller may be modified so that no suction control is provided. Alternatively, the suction control portion 109*b* may include an adapter 110 configured to fully or partially cover the opening 109*d* of the suction control portion 109*b*. For example, the adapter 110 may include a removable plug or similar device configured to be inserted into the opening 109*d* so as to partially or fully obstruct the opening 109*d*. Alternatively, the adapter may include a cover, which may be stationary or sliding for adjustable control, for partially or fully covering the opening 109*d*. The adapter can be used to provide consistent suction, with or without adjustment, through the suction tube, without requiring the user to use a finger to cover the opening 109*d*.

As shown in FIGS. 6A and 6C, the illumination control portion 109*a* extends from the suction control portion 109*b* and includes an elongated lever arm 109*a*1 that extends from an overmolded portion of the suction control portion 109*b* and at least one operation member or activation device 109*a*2 on the elongated arm 109*a*1. The elongated lever arm 109*a*1 may be flexible or semi-flexible so as to allow for up/down movement of the lever arm 109*a*1 within the handle upon pressing of the operation member 109*a*2. As discussed above, the operation member 109*a*2 in the present embodiment is a push button, but in other embodiments, the operation member 109*a*2 may be another suitable device capable of activating and deactivating and controlling the illumination assembly. In the illustrative embodiment of FIG. 6C, the push button 109*a*2 has a projection 109*a*3 that extends inwardly into the handle 105 from the lower surface of the button 109*a*2. When the button 109*a*2 is pressed by a user, the elongated lever arm 109*a*1 flexes and the projection 109*a*3 is pushed further into the handle 105 and engages with, or comes into contact with, a switch or a connection 212*a* on the PCB assembly 212 so that the pressing of the button 109*a*2 causes the activation or deactivation of the illumination assembly to turn the light source ON or OFF. Additional controls, such as brightness and/or hue adjustment may be programmed in the PCB so that the pressing of the button 109*a*2 causes the activation of a sequence of controls, each of which may be activated by a subsequent pressing of the button 109*a*2.

As can be seen in FIG. 6C and as discussed above, the button 109*a*2 extends through a second opening in the concave recessed portion 105*a*1 and is positioned so that its outer surface is at or below the outer surface of the concave recessed portion 105*a*1. In this way, inadvertent activation or deactivation of the illumination assembly, particularly during the suction control, is avoided.

FIG. 7A shows another embodiment of the illuminated suction device 700 of the present invention with a separately formed lens, and FIG. 7B shows an enlarged view thereof. In the illustrative example shown, the suction device 700 is a Frazier-type suction device. However, the suction device may be modified to be another type of suction device, such as Yankauer, Poole and/or Sigmoid suction devices. Moreover, the features of the suction device of the present embodiment, including an illumination assembly and a controller, may be used in, or modified for use in, other medical devices, such as retractors, laryngoscopes, electrocautery devices, speculums and other medical devices that use illumination and/or have components that produce heat.

As in the embodiment of FIGS. 1A-1E, the illuminated suction device 700 of FIGS. 7A-7B includes a suction tube 701 with a distal end 701*a* configured to be inserted into a wound or an incision and a proximal end fluidly coupled to a barb 702 or other suitable port for connecting to a suction source. The suction device 700 also includes an outer housing 704 which forms an ergonomic handle 705 for holding and manipulating the device and an elongated outer housing portion 706 extending from the handle 705 and covering at least a portion of the suction tube 701 and at least a portion of the illumination assembly provided in the suction device. The handle 705 is formed from rigid materials, while the elongated outer housing portion 706 is formed from flexible materials, which may be heat insulating materials and which do not add substantial thickness to the circumference of the device. For example, the elongated outer housing 706 may be formed from a flexible polymer or plastic, such as heat shrink tubing.

As in the embodiment of FIGS. 1A-1E, the suction device 700 of the present embodiment of FIGS. 7A-7B includes the illumination assembly with heat dissipation features and having a compact, low-profile construction which does not substantially increase the overall size of the device, particularly near its distal portion. As a result, the illumination assembly is suitable for use with suction devices and other medical devices that have limited available space thereon without affecting the viewability of a target operating site. As in the embodiments described above, the illumination assembly does not include a waveguide or a lightguide, thus delivering light directly emitted from the light source through a lens, minimizing loss of brightness. The suction device 700 also includes a controller 709 for controlling the illumination assembly and in certain embodiments, also for controlling the suction through the suction tube. As mentioned herein above, in some embodiments, such as when implemented in a Yankauer or other type of suction device, the suction control features may be omitted from the controller, or the controller may include an adapter or plug for at least partially obstructing a suction control opening in the controller. The controller 709 is provided in the handle 705 of the device 700 and is configured for ergonomic control of the illumination assembly and/or of the suction using one hand and, in some embodiments, using one finger.

In FIGS. 7A-7B, constructions of the suction tube 701, the housing 704, the controller 709 and the components within the handle 705, including electrical components, e.g., PCB assembly, the batteries, and the push-tab 708 or pull-tab, are similar or substantially the same as in the embodiments shown in FIGS. 1A-2B and 6A-6C, and thus, detailed descriptions thereof will be omitted. In the embodiment of FIGS. 7A-7B, construction of at least a portion of the illumination assembly, particularly, the constructions of components of the illumination assembly housed within the elongated outer housing portion 706 are different from the embodiments in FIGS. 1A-6C. The portions of the illumination assembly of FIGS. 7A-7B that are different from the embodiments shown in FIGS. 1A-6C are described in more detail below.

As shown in FIG. 7A and in more detail in FIG. 7B, the illumination assembly of this embodiment includes a heat sink 716 forming the spine of the illumination assembly, rather than having separately formed spine and heat sink. The heat sink 716 extends from the handle 705 at its proximal end along a portion of the suction tube 701 to a location offset from the suction tube's distal tip. The proximal end of the heat sink 716 may be positioned at a distal or proximal end of the handle 705 or may overlap with the handle. As can be seen in FIG. 7B, the surface of the heat sink 716 abutting the suction tube forms a channel or a concave-shaped surface, sized and shaped to receive the suction tube 701 so that the heat sink 716 sits on top of the suction tube 701 and extends partially around the suction tube. In other embodiments, the surface of the heat sink 716 may be shaped to form a space, e.g., air gap, between the heat sink 716 and the suction tube, and in some embodiments, a thermally insulating material may be provided between the heat sink 716 and the suction tube 701 to avoid heat transfer from the heat sink 716 to the suction tube 701. By having the heat sink 716 form the spine of the illumination assembly, the size of the heat sink 716 may be increased compared to the above-described embodiments in FIGS. 1A-6C to provide additional heat dissipation. Moreover, in the configuration shown in FIGS. 7A-7B, heat generated by the illumination can be absorbed by the heat sink 716 and then transferred away from the heat sink by the flow of air through the suction tube and by the elongated flexible housing 206 around the heat sink.

Additionally, in FIGS. 7A-7B, a lens 718 of the illumination assembly is formed separately from the spine and is attachable to a distal end of the heat sink 716 that forms the spine. By forming the lens 718 separately from the spine/heat sink 716, the lens can be formed from different materials than the spine/heat sink 716 and can be permanently attached to the spine/heat sink 716 or releasably attached to the spine/heat sink 716. In certain embodiments, the lens 718 is releasably attached to the spine/heat sink 716 and may be interchanged with other lenses that may have different refractive characteristics.

As shown in FIG. 7B, the lens 718 includes a light receiving portion 718*a* forming the lens and a pair of side arms 718*b*, each extending from a side of light receiving portion 718*a* for attaching the lens 718 to the heat sink 716. The light receiving portion 718*a* may be an aspheric lens or any other suitable lens. For example, lenses described above with respect to FIGS. 1A-6C may be used in the lens 718 of this embodiment. The side arms 718*b* extend from the light receiving portion 718*a* towards the heat sink 716 and are configured to overlap with the heat sink 716 and to snap fit connect with the heat sink 716. In the illustrative embodiment shown in FIG. 7B, each side arm 718*b* has a snap fit projection 718*c* on its inner surface which is configured to engage with a corresponding snap recessed surface 716*a* on the heat sink 716. In some embodiments, each side arm 718*b* may have a recess on its inner surface configured to engage with a corresponding projection on the surface of the heat sink 716. It is understood that other types of coupling between the lens 718 and the heat sink 716 may be used, including but not limited to, using adhesives, welding, ultrasound welding, using various fasteners, etc.

As shown in FIG. 7B, the overall shape of the light receiving portion 718*a* of the lens conforms to the cross-sectional shape of the distal end of the heat sink 716 so that when the lens 718 is attached to the heat sink 716, the light receiving portion 718*a* covers the distal end of the heat sink 716. As can be seen in FIG. 7B, lower surface of the light receiving portion 718*a* of the lens that faces the suction tube is shaped to conform to the shape of the suction tube, and in this illustrative embodiment, is concave. When the lens 718 is coupled to the heat sink 716, a space is formed between the light receiving portion 718*a* of the lens 718 and the distal end surface of the heat sink 716 for accommodating one or more direct light sources 720 and for providing predetermined space between one or more direct light sources 720 and the light receiving portion 718*a* of the lens. In this embodiment, the interface between the lens 718 and the heat sink 716 is sealed so as to prevent fluids from entering the space between the lens 718 and the heat sink 716. In this illustrative embodiment, the sealing is provided by a gasket 718*d* formed around a periphery of the light receiving portion 718*a* of the lens 718. Specifically, in FIG. 7B, the gasket 718*d* is formed by a peripheral projection on an inner surface of the light receiving portion 718*a* that abuts the distal end of the heat sink 716, and the distal end of the heat sink 716 includes a corresponding peripheral gasket mate surface 716*b* configured to engage with or mate with the peripheral projection on the light receiving portion 718. In other embodiments, other methods of sealing may be used, including using a separately formed gasket at the interface between the lens 718 and the heat sink 716, using silicone or other sealing coatings or gaskets at the interface between the lens 718 and the heat sink 716, using ultrasonic welding to form the seal around the periphery of the lens 718 and the distal end of the heat sink 716, using glue to seal the interface between the lens 718 and the heat sink 716, using molded thermoplastic elastomers (TPE) to form the gasket, and other suitable methods.

As shown in FIG. 7B, the illumination assembly includes at least one direct light source 720, such as a LED or any other suitable light source, mounted on a flexible circuit 721, such as a flexible PCB described above. In the embodiment of FIG. 7B, the direct light source 720 is positioned at the distal end of the heat sink 716 and is thermally coupled to the heat sink 716 so that heat produced by the direct light source 720 is absorbed and dissipated by the heat sink 716. In some embodiments, the light source 720 directly abuts the distal end of the heat sink 716, while in other embodiments a thermal conductor, such as thermally conductive tape, may be used between the light source 720 and the heat sink 716. In some embodiments, the flexible circuit 721 on which the light source 720 is mounted wraps around the heat sink 716, similarly to the above-described embodiments in FIGS. 3A-3C, with a first free end of the flexible circuit 721 extending adjacent one surface of the heat sink 716 for a relatively short distance and the second free end thereof extending adjacent an opposing surface of the heat sink 716 to the handle to electrically connect with the control assembly, e.g., PCB control assembly. In other embodiments, the first free end of the flexible circuit 721 may be attached to the distal end of the heat sink 716, such as by using adhesives, tape or other suitable coupling, or may be inserted into a slot formed within the heat sink 716 to hold the first free end of the flexible circuit 721 in place. In such embodiments, the second free end of the flexible circuit 721 extends along the heat sink 716 to the handle for electrical connection with the control assembly. It is understood that in some embodiments, wiring may be used for electrically connecting the light source 720 with the control assembly instead of the flexible circuit. In addition, in some embodiments, multiple light sources may be used in the illumination assembly and the light sources may be positioned at the distal end of the heat sink 716 and/or along a portion of the length of the heat sink 716 so as to provide illumination in different directions.

As mentioned above, the elongated outer housing portion 706, shown in FIG. 7A as separated from the suction device, is applied to enclose the heat sink 716 and a portion of the suction tube 701. The elongated outer housing 706 may be made from flexible or semi flexible material, such as a heat shrinking tube, and may be applied using heat shrinking or other suitable methods to wrap around and to at least partially enclose the heat sink 716 and the portion of the suction tube 701.

While various features and variations thereof have been described with respect to suction devices, it is noted that one or more of the features described herein may be embodied within other medical devices which include an illumination assembly, including but not limited to retractors, speculums, anoscopes, laryngoscopes, cannula and others. The specific configurations of the LED arrangement, flexible circuit board, optical elements (spine and lens), heat sink or the push-tab assembly may be modified, as needed, for the specific device in which is it used.

In all cases, it is understood that the above-described arrangements are merely illustrative of the many possible specific embodiments which represent applications of the present invention. Numerous and varied other arrangements, including use of different materials and various configurations of components of the suction device, can be readily devised without departing from the spirit and scope of the invention.

We claim:

1. A suction device comprising:

a suction tube configured to fluidly couple to a vacuum source and to provide suction at a distal end of the suction tube; and an illumination assembly comprising:

at least one direct light source for emitting light to a target area;

an elongated heat sink thermally coupled to the at least one direct light source and extending along a portion of the suction tube;

a flexible circuit to which the at least one direct light source is connected, wherein the flexible circuit wraps around a first edge of a distal-facing surface of the elongated heat sink and a second, opposite edge of the distal-facing surface of the elongated heat sink to secure a position of the at least one direct light source with respect to the suction tube;

a spine extending along the suction tube, overlapping with the elongated heat sink, and with a majority of the spine being enclosed within an interior region of an outer housing of the suction device; and a lens connected to the spine for refracting the light emitted from the at least one direct light source, wherein the at least one direct light source and the elongated heat sink are enclosed within a space formed between the spine and a side of the suction tube.

2. The suction device in accordance with claim 1, wherein the spine is transparent or translucent.

3. The suction device in accordance with claim 1, wherein the lens is integrated into a distal end of the spine or connected to the distal end of the spine, and wherein the lens is configured to refract the light emitted from the at least one direct light source toward the target area.

4. The suction device in accordance with claim 1, wherein the lens is an aspherical lens.

5. The suction device in accordance with claim 1, wherein the spine includes an elongated channel, and wherein the at least one direct light source and the elongated heat sink are positioned within the elongated channel.

6. The suction device in accordance with claim 1, wherein the at least one direct light source is mounted on the flexible circuit, wherein the flexible circuit includes electrical connections, and wherein the flexible circuit wraps around the elongated heat sink to position the at least one direct light source adjacent the distal-facing surface of the elongated heat sink.

7. The suction device in accordance with claim 6, wherein the at least one direct light source is mounted on the flexible circuit at a predetermined distance from a first free end of the flexible circuit, wherein the first free end of the flexible circuit and a first portion of the flexible circuit extend along a first surface of the elongated heat sink, wherein a second portion of the flexible circuit extends along a second, opposing surface of the elongated heat sink, and wherein the second portion of the flexible circuit electrically connects the at least one direct light source to a power source.

8. The suction device in accordance with claim 1, wherein an inner surface of the spine abuts a first surface of the elongated heat sink; and wherein:

the elongated heat sink includes a recess in a first surface of the elongated heat sink and the spine includes a respective projection on the inner surface of the spine, and the recess is positioned so as to engage with the respective projection; or the elongated heat sink includes a projection in the first surface of the elongated heat sink and the spine includes a respective recess on the inner surface of the spine, and the projection is positioned so as to engage with the respective recess.

9. The suction device in accordance with claim 1, further comprising:

a handle enclosing a proximal end of the suction tube;

at least one power source; and a control assembly for controlling an operation of the illumination assembly, wherein the handle at least partially encloses the at least one power source and the control assembly.

10. The suction device in accordance with claim 1, wherein the outer housing encloses at least a portion of the suction tube.

11. The suction device in accordance with claim 1, wherein the at least one direct light source is positioned at a distal-facing portion of the flexible circuit.

12. The suction device in accordance with claim 1, wherein the at least one direct light source is oriented substantially perpendicularly to an elongate axis of the flexible circuit.

13. The suction device in accordance with claim 1, wherein the at least one direct light source is oriented substantially perpendicularly to an elongate axis of the elongated heat sink.

14. The suction device in accordance with claim 1, wherein the suction device does not include a light guide.

15. The suction device in accordance with claim 1, wherein a first portion of the flexible circuit extends away from the first edge of the distal-facing surface in a direction and a second portion of the flexible circuit extends away from the second, opposite edge of the distal-facing surface in the same direction.

16. The suction device in accordance with claim 15, wherein the first and second portions of the flexible circuit extend along a longitudinal axis of the elongated heat sink.

17. The suction device in accordance with claim 15, wherein a third portion of the flexible circuit extends between the first portion and the second portion and is substantially centered on the distal-facing surface of the elongated heat sink.

18. The suction device in accordance with claim 15, wherein one of the first portion and the second portion extends along an upper side of the elongated heat sink and the other of the first portion and the second portion extends along a lower side of the elongated heat sink.

19. The suction device in accordance with claim 15, wherein the first portion has a first length and the second portion has a second length that is different from the first length.

20. The suction device of claim 1, wherein the outer housing extends along at least a portion of the suction tube and surrounds a circumference of the suction tube along an entire exposed length of the outer housing.

* * * * *